(12) United States Patent
Le Clainche et al.

(10) Patent No.: US 9,234,001 B2
(45) Date of Patent: Jan. 12, 2016

(54) CYSTEINE-FREE EFFICIENT TECHNETIUM (TC) OR RHENIUM (RE) CHELATING PEPTIDE TAGS AND THEIR USE

(75) Inventors: Loïc Le Clainche, Montrouge (FR); Alain Lecoq, Mennecy (FR); Sophie Zinn-Justin, Gif-sur-Yvette (FR); Robert Thai, Nozay (FR); Michel Masella, Asnieres (FR); Philippe Cuniasse, Montrouge (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 806 days.

(21) Appl. No.: 13/133,446

(22) PCT Filed: Dec. 28, 2009

(86) PCT No.: PCT/IB2009/007971
§ 371 (c)(1),
(2), (4) Date: Sep. 12, 2011

(87) PCT Pub. No.: WO2010/076654
PCT Pub. Date: Jul. 8, 2010

(65) Prior Publication Data
US 2011/0318827 A1  Dec. 29, 2011

(30) Foreign Application Priority Data
Dec. 30, 2008 (EP) .................................... 08291257

(51) Int. Cl.
| | | |
|---|---|---|
| C07K 7/06 | (2006.01) | |
| C07K 5/083 | (2006.01) | |
| C07K 5/062 | (2006.01) | |
| C07K 5/09 | (2006.01) | |
| C07K 5/103 | (2006.01) | |
| C07K 7/08 | (2006.01) | |

(52) U.S. Cl.
CPC ........... *C07K 5/0806* (2013.01); *C07K 5/06026* (2013.01); *C07K 5/081* (2013.01); *C07K 5/0815* (2013.01); *C07K 5/1013* (2013.01); *C07K 7/06* (2013.01); *C07K 7/08* (2013.01)

(58) Field of Classification Search
None
See application file for complete search history.

(56) References Cited

U.S. PATENT DOCUMENTS 4,421,735 A * 12/1983 Haber et al. ................. 424/1.45
6,884,776 B1 * 4/2005 Nibbering et al. ............ 514/2.3

FOREIGN PATENT DOCUMENTS

EP  0 403 225 A2  12/1990
WO  WO 98/54314 A1  12/1998

OTHER PUBLICATIONS

Lam et al., "A One-Bead One-Peptide Combinatorial Library Method for B-Cell Epitope Mapping", Methods: A Companion to Methods in Enzymology, 1996, pp. 482-493.*
Brouwer et al.,"Synthetic peptides derived from human antimicrobial peptide ubiquicidin accumulate at sites of infections and eradicate (multi-drug resistant) *Staphylococcus aureus* in mice", Peptides, 2006, pp. 2585-2591.*
Ferro-Flores et al., "In vitro and in vivo assessment of 99mTc-UBI specificity for bacteria", Nuclear Medicine and Biology, 2003, pp. 597-603.*
Brouwer et al., "The Use of Technetium-99m Radiolabeled Human Antimicrobial Peptides for Infection Specific Imaging", Mini-Reviews in Medicinal Chemistry, 2008; pp. 1039-1052.*
Welling et al., "Radiochemical and biological characteristics of 99mTc-UBI 29-41 for imagining of bacterial infections", Nuclear Medicine and Biology, 2002, pp. 413-422.*
International Search Report and Written Opinion for Application No. PCT/IB209/007971 dated Oct. 27, 2010.
Ferro-Fores, G. et al., *Molecular Recognition and Stability of $^{99m}Tc$-UBI 29-41 based on Experimental and Semiempirical Results*, Applied Radiation and Isotopes 61 (2004) 1261-1268.
Melendez-Alafort, L. et al., *Lys and Arg in UBI: A Specific Site for a Stable $^{99m}Tc$-99 complex?*, Nuclear Medicine and Biology 30 (2003) 605-615.
Welling, M. M. et al., *Radiochemical and Biological Characteristics of $^{99m}Tc$-UBI 29-41 for Imaging of Bacterial Infections*, Nuclear medicine and Biology 29 (2002) 413-422.
Welling, M. M. et al., *Nucl Med Biol* 2002, 29, 413-22.
Ferro-Flores, G. et al., *Appl Radiat Isot* 2004, 61, 1261-8.
Melendez-Alafort, L. et al., *Nucl Med Biol* 2003, 30, 605-15.
Bogdanov, A., Jr., et al., *Biochim Biophys Acta* 1998, 1397, 56-64.
Tait, J. F. et al., *Bioconjug Chem* 2000, 11, 918-25.
Levashova, Z. et al., *Bioconjug Chem* 2008, 19, 1049-54.
Waibel, R. et al., *Nat Biotechnol* 1999, 17, 897-901.
Nilges, M. et al., *FEBS Lett* 1988, 239, 129-36.
Schwieters, C. D. et al., *Magn Reson* 2003, 160, 65-73.
Boyd, G. E., *J. Chem Ed* 1959, vol. 36, pp. 3-12.
Rustom, R. et al., *Clin. Sci (Lond)* 1992, 83(3), 289-294.
Merrifield, R. B., *Solid Phase Peptide Synthesis. I. The Synthesis of a Tetrapeptide*, J. Am. Chem. Soc. 85 (14): 2149-2154.
Bodansky, M. et al., *The Practice of Peptide Synthesis*, 1984, Springer-Verlag.
Liebow, C. et al., *Somatostatin Analogues Inhibit Growth of Pancreatic Cancer by Stimulating Tyrosine Phosphatase*, Pro Natl Acad Sci USA 1989, 86, Jul. 2003.
Reubi, J. C. et al., *Somatostatin Receptor sst1-sst5 Expression in Normal and Neoplastic Human Tissues Using Receptor Autoradiography With Subtype-Selective Ligands*, Eur J Nucl Med 28, 2001, 836-46.

* cited by examiner

*Primary Examiner* — Karlheinz R Skowronek
*Assistant Examiner* — Lianko Garyu
(74) *Attorney, Agent, or Firm* — Alston & Bird LLP

(57) ABSTRACT

The present invention relates to a peptide tag which can be used to bind a Technetium (Tc) or Rhenium (Re) radionuclide to a protein of interest which comprises the peptide tag and allows the imaging of such a tagged protein. In particular the present invention relates to a peptide tag which chelates a Tc or Re atom but which does not comprise a Cysteine residue.

3 Claims, 4 Drawing Sheets

Figure 1:
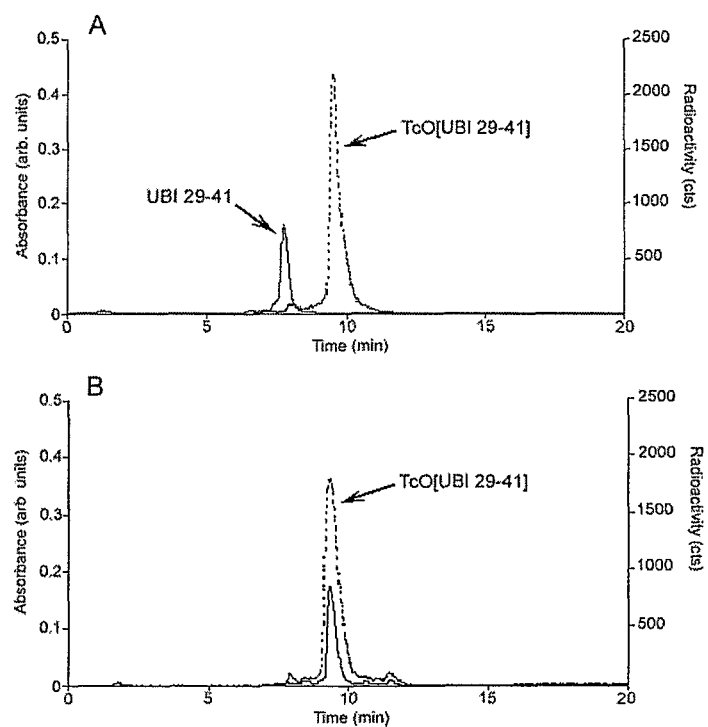

RC-121:

$_D$Phe Cys Tyr $_D$Trp Lys Val Cys Thr$_{NH2}$   (SEQ ID NO :40)

(disulfide bond between the two Cys residues)

$_H$TGRRRGG-RC-121:

Thr Gly Arg Arg Arg Gly Gly $_D$Phe Cys Tyr $_D$Trp Lys Val Cys Thr$_{NH2}$ (SEQ ID NO :41)

(disulfide bond between the two Cys residues)

Figure 3

CYSTEINE-FREE EFFICIENT TECHNETIUM (TC) OR RHENIUM (RE) CHELATING PEPTIDE TAGS AND THEIR USE

FIELD OF THE INVENTION

The present invention relates to a peptide tag which can be used to bind a radionuclide to a protein of interest which comprises the peptide tag and allows the imaging of such a tagged protein. In particular the present invention relates to a peptide tag which chelates a Tc or Re atom but which does not comprise a Cysteine residue as well as to vectors incorporating the tag and to chemical methods to join the tag to an existing protein.

BACKGROUND OF THE INVENTION

The radio labelling of antibodies, proteins or peptides to produce efficient imaging agents remains a very important goal in the field of molecular imaging which is presently hindered by the lack of suitable compounds.

The natural ability of native molecules to target their antigens or receptors could lead to highly specific imaging or therapeutic molecules due to their innate affinity and specificity. Imaging agents could, in principle, be obtained from such peptides or proteins via their labelling with an element possessing a property that renders these labelled molecules detectable with an imaging system.

Among the various methods developed, radio labelling with $^{99m}Tc$ has been long recognized as a very attractive approach. $^{99m}Tc$ is a metastable nuclear isotope of technetium-99, which has almost ideal properties for in vivo diagnostic imaging. It has a half life (about 6 h) which is long enough to allow the preparation of an imaging agent and for the diagnostic studies to be performed, but is short enough to permit the administration of millicurie amounts without exposing the patient to a significant dose of irradiation.

The monochromatic 140 Key photons and its 89% abundance are ideal for imaging studies with gamma cameras or SPECT systems. In addition, $^{99m}Tc$ can be easily obtained from $^{99}Mo/^{99m}Tc$ generator taking advantage of the transient equilibrium between the parent radionuclide $^{99}Mo$ and the $^{99m}Tc$ radionuclide. The separation of $^{99}Mo$ and $^{99m}Tc$ is easily achieved from the generator by elution of pertechnetate $TcO_4^-$ with saline solutions.

The Tc cores can then be prepared by reduction of the eluted pertechnetate. Several oxidation states of Tc can be generated and used. One of the most studied core corresponds to diatomic Tc(V) core $[TcO]^{3+}$ and more recently a number of studies reported the production and use of the Tc(I) triscarbonyl $[Tc(CO)_3]^+$ to label peptides and proteins.

Rhenium has similarly advantageous properties which make it a suitable element for radiolabelling and in vivo/in vitro imaging and therapeutic uses. In addition Re and Tc have very similar chemistry and as Re is less expensive to produce and certain of its isotopes have a longer half-life than Tc, this could make Rc a better radionuclide for some uses.

Several strategies have already been proposed to radiolabel peptides and proteins with technetium or rhenium:

A first method corresponds to the so-called direct method, which involves the reduction of disulfide bridges present in the molecule of interest and the chelation of the Tc core to the resulting sulfudryl groups (1). While this first method appears simple and easy to perform, it has a number of limitations (2). The first one concerns the impact of chelation on the structure of the protein, normally disulfide bridges play an important role in forming and maintaining the correct folding/structure of a protein and therefore its binding capacity to the targeted receptor. By disrupting the disulfide bridges the resulting labelled protein can lack affinity for its target. Furthermore, the chelated Tc core may interact with or be positioned in the binding region of the protein of interest resulting in the partial or total loss of its biological activity.

A second, indirect method has been proposed to label protein and peptides with Tc cores using a bifunctional chelating agent (BFCA). This method is based on the chemical grafting of strong Tc core chelators onto the surface of the protein by a chemoselective reaction that most often involves Lysine residues. One of the most widely used chelator is the HYNIC group (hydrazinonicotinamide) (3,4). While the presence of such a strong chelator increases the labelling yield and the resulting stability of the Tc complexes formed, the major drawback of this method is that it offers no control on the location of the BFCA on the surface of the protein, which thus can lead to a pool of heterogenous labelled molecules a subset of which may have reduced binding capacity and in any event make quantitative and repeatable studies difficult.

A third approach, called preformed chelate has been proposed to label antibodies (5, 6). However, this approach suffers from the same limitations as the direct and the indirect approaches regarding the absence of control over the location of the preformed Tc-Chelate complex that reacts with any Lysine residues present.

Site specific labelling of proteins with Tc or Re using peptide tag sequences has been proposed as an alternative to the methods described above. This approach consists of adding at a N-terminal or C-terminal position of the protein of interest, a peptide sequence able to chelate a Tc/Re core. Several peptide sequences have been described as $[TcO]^{3+}$ chelators (7). These peptides form square pyramidal oxotechnetium complexes with tetradentate chelators. The majority of the reported natural amino acid containing peptides possess a Cysteine residue that participates in the chelation via its thiolate group.

Examples of this type of peptide tag are the Gly-Gly-Cys (SEQ ID NO: 28) and the Lys-Gly-Cys (SEQ ID NO: 29) sequences with a N3S chelating motif and the Cys-Gly-Cys (SEQ ID NO: 30) with a N2S2 motif (8, 9). It is however known in the art that the presence of an unpaired Cysteine may interfere in the folding processes of a protein and therefore reduce the yield of production of the modified protein or alter its final conformation. An unpaired Cysteine may also lead to alteration of the targeting molecule during storage.

$[TcO]^{3+}$ chelating-peptide sequences containing proteinogenic amino acids but without Cysteine residues would therefore appear to be good candidate molecules. However, such peptide sequences are extremely uncommon and in the art only peptide sequences containing Glycine and Alanine residues have been shown to be able to chelate the $[TcO]^{3+}$ core in a N4 motif (10, 11). These peptides showed interconverting $[TcO]^{3+}$ syn and anti isomers and no stability data has been reported for these complexes prior to in vivo testing. Stability is an essential property of a radio-labelled reagent as dissociated $[TcO]^{3+}$ complexes will result in a greater non-specific background signal leading to a lower signal to noise ratio.

In addition, it was recently demonstrated that the [AGGG] TcO complex (SEQ ID NO: 31) was completely unstable against 30 equivalents of Cysteine (12).

Recently dipeptide sequences have been proposed as TcO/ReO chelating sequence (13). These dipeptides have the major disadvantage that they comprise only three Tc/Re chelating functional groups, which would be expected to impact upon the stability of the complex, thereby reducing their usefulness for in vivo applications.

SUMMARY OF THE INVENTION

The identification of novel efficient $[TcO]^{3+}$ chelating peptide sequences incorporable in proteins either by peptide chemistry or molecular biology remains therefore an important challenge for the development of imaging agents.

Therefore according to a first aspect of the present invention there is provided the use of a peptide tag selected from the group consisting of:

a) $X_a X_1 X_2 X_3 X_4 X_5 X_b X_c$,
wherein
  $X_a$ or $X_c$ when present comprise at least two amino acids and link said peptide tag to a protein of interest,
  $X_b$ when present comprises the peptide sequence RRMQYNRR (SEQ ID NO: 38) in which at least one of said residues is replaced with a non-natural or natural amino acid in which at least one side chain present in the native residue which it replaces is absent,
  $X_1$ consists of any amino acid comprising an OH group upon its side chain; in particular $X_1$ is selected from the group comprising: Threonine, Serine, Aspartic acid, Glutamic acid.
  $X_2$ consists of any amino acid except for Cysteine,
  $X_3$ consists of an amino acid selected from the group consisting of: Arginine, Glycine, Lysine,
  $X_4$ consists of at least one amino acid which is either Alanine, Glycine, Lysine or Arginine,
  $X_5$ comprises at least one amino acid except for Cysteine;
b) the retro-inverso version of a peptide tag according to group a); for the radio labelling of a protein of interest with a Tc or Re radionuclide.

DETAILED DESCRIPTION

In the present invention, chelation means the binding of the Tc/Re core to a bi- or multidentate ligand, which in accordance with the present invention is the peptide or protein to be labelled.

The inventors have investigated in detail the $[TcO]^{3+}$ labelling of the peptide UBI 29-41 (SEQ ID NO: 1). This peptide is a tridecamer corresponding to residue 29 to 41 of the protein Ubiquicidine, originally isolated from mouse macrophages (14). UBI 29-41 is a cationic antimicrobial peptide of the sequence TGRAKRRMQYNRR (SEQ ID NO: 1) possessing five Arginine residues and one Lysine.

Despite the absence of a Cysteine residue, UBI 29-41 was previously labelled by a direct approach with a specific activity and an in vitro and in vivo stability enabling its use as imaging agent (15-17). However, none of the labelling studies reported experimental data allowing the unambiguous identification of the $[TcO]^{3+}$ core chelation site in UBI 29-41. In the absence of experimental data, it has however been proposed on the basis of semi empirical calculations, that the TcO core could be chelated via Arginine 7 or Lysine 5 side chain residues in UBI 29-41 (18).

The inventors findings disprove the proposal of Ferro-Flores et al. (18) that the $[TcO]^{3+}$ core was coordinated via the Lysine 5 and Arginine 7 side chain chemical functions. In this respect, the inventors have shown that the replacement of residue K5 by a Norleucine residue (Analog UBI-A3, Table I) and that of R7 by a Norvaline (Analog UBI-A5, Table I) do not lead to any decrease in the labelling yield clearly showing that these residues were not directly involved in the coordination of the $[TcO]^{3+}$ core.

Instead the inventors have shown that the first four residues $X_1 X_2 X_3 X_4$, corresponding to the sequence $T_1 G_2 R_3 A_4$ in UBI 29-41, have the greatest impact upon chelation. In particular they have found that the OH group present in the side chain of the native Threonine residue ($X_1$) plays a very important role in the chelation of the radionuclide. Based upon these findings the inventors have developed a set of peptide tags which can be used to chelate a $[TcO]^{3+}$ core which are of a smaller size than UBI 29-41 and which have a labelling yield of comparable or greater efficiency with $[TcO]^{3+}$ cores and or peptide tags which are of comparable size to UBI 29-41 but which have a significantly greater labelling yield to $[TcO]^{3+}$ cores.

The peptide tag may further comprise a linker at its N or C terminal so as to facilitate the incorporation of the tag into a protein of interest at the C or N terminal thereof respectively. It is known in the art that additions to a protein sequence at the C or N terminus can lead to unexpected and unwanted conformational and/or functional changes in the protein. To alleviate such problems a peptide linker can be used to link the native functional domain of the protein, located at the C or N terminus, to the new functional domain. Such peptide linkers normally comprise a string of several amino acid residues which are not expected to affect either the native or new functional domains. Examples include a series of six Histidine residues or two Glycine residues, but many other linkers are known in the art of various lengths and amino acid composition.

Further the peptide tag may comprise a further portion of UBI 29-41, corresponding to residues 5 to 13 thereof, which the inventors have shown when at least one residue therein is replaced with a non-natural or natural amino acid residue lacking the side chain of the native residue leads to an increase in radionuclide labelling of the peptide tag.

These radio-labelled proteins may be used for a variety of purposes such as in vitro and in vivo imaging and radiotherapy.

In particular $X_5$ comprises Norleucine.
In particular $X_2$ is Glycine.
In particular the peptide tags are selected from the following:
(SEQ ID NO: 14); (SEQ ID NO: 15); (SEQ ID NO: 16); (SEQ ID NO: 17); (SEQ ID NO: 18); (SEQ ID NO: 19); (SEQ ID NO: 20); (SEQ ID NO: 21); (SEQ ID NO: 22); (SEQ ID NO: 23); (SEQ ID NO: 24); (SEQ ID NO: 25); (SEQ ID NO: 26); (SEQ ID NO: 27) (SEQ ID NO: 34); (SEQ ID NO: 39); (SEQ ID NO: 2); (SEQ ID NO: 3); (SEQ ID NO: 4); (SEQ ID NO: 5); (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13).

The inventors have also shown that the retro-inverso version of the peptide tags which they have developed, that is peptides which contain NH—CO bonds instead of CO—NH peptide bonds, have similar properties. In addition retro-inverso peptides are much more resistant to proteolysis than L-peptides and hence better candidate molecules for in vitro and in vivo imaging reagents. Such retro-inverso peptides can be incorporated into the terminus of the protein to be labelled.

In particular the tag comprises a free N-terminus on the N-terminal residue.

The inventors have shown that peptide tags with a free N-terminus, that is with a free amine group, show higher levels of $[TcO]^{3+}$ core chelation than those lacking a free N-terminus.

In particular the peptide tag comprises a free carboxylate on the C-terminal residue.

In particular the Tc radionuclide is $^{99m}$Tc.

In particular the Re radionuclide is $^{186}$Re or $^{188}$Re.

According to this aspect of the present invention there is also provided a method to radio label a protein of interest comprising the steps of:

1) incorporating into said protein of interest a peptide tag selected from the group consisting of a) $X_aX_1X_2X_3X_4X_5X_bX_c$, wherein $X_a$ or $X_c$ when present comprise at least two amino acids and link said peptide tag to a protein of interest, $X_b$ when present comprises the peptide sequence RRM-QYNRR (SEQ ID NO: 38) in which at least one of said residues is replaced with a non-natural or natural amino acid in which at least one side chain present in the native residue which it replaces is absent, $X_1$ consists of any amino acid comprising an OH group upon its side chain; in particular $X_1$ is selected from the group comprising: Threonine, Serine, Aspartic acid, Glutamic acid.

$X_2$ consists of any amino acid except for Cysteine, $X_3$ consists of an amino acid selected from the group consisting of Arginine, Glycine, Lysine, $X_4$ consists of at least one amino acid which is either Alanine, Glycine, Lysine or Arginine, $X_5$ comprises at least one amino acid except for Cysteine;

b) the retro-inverso version of a peptide tag according to group a) and, 2) chelating a Tc or Re radionuclide with the resulting product of step 1).

In addition this first aspect of the present invention also relates to isolated or purified nucleotide molecules encoding one or more of the peptide tags according to this first aspect of the present invention.

According to a second aspect of the present invention there is provided a vector characterised in that it comprises a coding sequence for a peptide tag according to the first aspect of the present invention; a cloning site configured to introduce a protein coding sequence in frame with said peptide tag forming a fusion protein; and the transcriptional elements necessary to express said fusion protein in a target cell or cell free expression system.

A vector, otherwise known as an expression vector or expression construct, is generally a plasmid that is used to introduce a specific gene into a target cell. Once the vector is inside the cell, the protein that is encoded by the gene is produced by the cellular-transcription and translation machinery. The plasmid is frequently engineered to contain regulatory sequences that act as enhancer and promoter regions and lead to efficient transcription of the gene carried on the vector. The goal of a well-designed vector is the production of large amounts of stable messenger RNA which in turn is translated into the gene product.

After expression of the gene product, the purification of the protein maybe required and it can be purified from the proteins of the host cell. To make the purification process easy, the cloned gene may have a tag as a multiple histidine (His) tag or any other suitable small detectable peptide sequence.

The arrangement of the cloned coding sequence of the protein of interest so that it is in frame with the selected peptide tag, may be performed in accordance with standard molecular biology techniques and in particular in accordance with Molecular Cloning: A Laboratory Manual (Third Edition) by Joseph Sambrook, and David Russell (ISBN 978-087969576-7).

In particular according to this aspect of the present invention the vector may be able to drive the expression of the protein comprising a peptide tag, in at least one eukaryotic and/or prokaryotic cell.

Alternatively according to this aspect of the present invention the vector may be able to drive the expression of the protein comprising a peptide tag, in at least one cell free expression system.

According to a third aspect of the present invention there is provided a method to synthesis a peptide tag according to the first aspect of the present invention, wherein said peptide tag is synthesised by liquid phase (41) or solid phase peptide synthesis (SPPS) (40).

Peptides are synthesized by coupling the carboxyl group or C-terminus of one amino acid to the amino group or N-terminus of another. The possibility of unintended reactions is obvious, thus protecting groups are usually necessary. Generally peptide synthesis methods are conducted in the liquid phase or solid phase.

In SPPS, small solid beads, insoluble yet porous, are treated with functional units ('linkers') on which peptide chains can be built. The peptide will remain covalently attached to the bead until cleaved from it by a cleaving reagent. The peptide is thus 'immobilized' on the solid-phase and can be retained during a filtration process, whereas liquid-phase reagents of synthesis are flushed away.

This method is based upon repeated cycles of coupling-deprotection. The free N-terminal amine of a solid-phase attached peptide is coupled to a single N-protected amino acid unit. This unit is then deprotected, revealing a new N-terminal amine to which a further amino acid may be attached.

Many variations exist in the art upon these peptide synthesis methods and these are encompassed by the present invention.

In the present invention both the peptide tag and a protein comprising the peptide tag can be synthesised for further use.

According to a fourth aspect of the present invention there is provided a method to synthesis a protein comprising a peptide tag according to the first aspect of the present invention, wherein said protein is synthesised by liquid phase or solid phase synthesis.

According to a fifth aspect of the present invention there is provided a method to chemically link a peptide tag according to the first aspect of the present invention to a target protein, comprising the steps of:

a) activating a purified sample of said target protein with an activating agent;

b) activating a purified sample of said peptide tag with an activating agent;

c) incubating the products of step a) and step b) and purifying peptide tag-target protein complexes.

Similar techniques to liquid phase peptide synthesis can be used to attach a peptide tag to a protein of interest in vitro by using ligation or crosslinking techniques. Other coupling methods exist in the art and are encompassed by the present invention.

According to a sixth aspect of the present invention there is provided an isolated or purified peptide tag selected from the group consisting of:

a) $X_aX_1X_2X_3X_4X_5X_bX_c$, wherein $X_a$ when present comprises at least two amino acids and consists of a peptide sequence other than KVAKQEKKKKK (SEQ ID NO: 43) and links said peptide tag to a protein of interest, $X_b$ when present comprises the peptide sequence RRM-QYNRR (SEQ ID NO: 38) in which at least one of the residues is replaced with a non-natural or natural amino acid in which at least one side chain present in the native residue which it replaces is absent, $X_c$ when present comprises at least two amino acids and consists of a peptide sequence other than RRMQYNRR (SEQ ID NO: 38) and links said peptide tag to a protein of interest, $X_1$ consists of any amino acid comprising an OH group upon its side chain, $X_2$ consists of any amino acid except for Cysteine, $X_3$ consists of an amino acid selected from the group consisting of: Arginine, Glycine, Lysine, $X_4$ consists of at least one amino acid which is either Alanine, Glycine, Lysine or Arginine, $X_5$ comprises at least one amino acid except for Cysteine;

b) the retro-inverso version of a peptide tag according to group a).

In particular $X_5$ comprises Norleucine.

In particular $X_1$ is selected from the group comprising: Threonine, Serine, Tyrosine, Aspartic acid, Glutamic acid.

In particular $X_2$ is Glycine.

In particular the peptide tags are selected from the following:

(SEQ ID NO: 14); (SEQ ID NO: 15); (SEQ ID NO: 16); (SEQ ID NO: 17); (SEQ ID NO: 18); (SEQ ID NO: 19); (SEQ ID NO: 20); (SEQ ID NO: 21); (SEQ ID NO: 22); (SEQ ID NO: 23); (SEQ ID NO: 24); (SEQ ID NO: 25); (SEQ ID NO: 26); (SEQ ID NO: 27); (SEQ ID NO: 34); (SEQ ID NO: 39); (SEQ ID NO: 2); (SEQ ID NO: 3); (SEQ ID NO: 4); (SEQ ID NO: 5); (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13).

According to a seventh aspect of the present invention there is provided an isolated or purified peptide tag chelated with a Tc core, wherein said peptide tag is selected from the group consisting of a) $X_aX_1X_2X_3X_4X_5X_bX_c$, wherein $X_a$ when present comprises at least two amino acids and consists of a peptide sequence other than KVAKQEKKKKK (SEQ ID NO: 43) and links said peptide tag to a protein of interest, $X_b$ when present comprises the peptide sequence RRMQYNRR (SEQ ID NO: 38) in which at least one of the residues is replaced with a non-natural or natural amino acid in which at least one side chain present in the native residue which it replaces is absent, $X_c$ when present comprises at least two amino acids and consists of a peptide sequence other than RRMQYNRR (SEQ ID NO: 38) and links said peptide tag to a protein of interest, $X_1$ consists of any amino acid comprising an OH group upon its side chain, $X_2$ consists of any amino acid except for Cysteine, $X_3$ consists of an amino acid selected from the group consisting of: Arginine, Glycine, Lysine, $X_4$ consists of at least one amino acid which is either Alanine, Glycine, Lysine or Arginine, $X_5$ comprises at least one amino acid except for Cysteine;

b) the retro-inverso version of a peptide tag according to group a).

The Inventors have shown that the peptide tags they have developed can be stably chelated with a Tc core.

In particular the chelated Tc core is $(TcO)^{3+}$ or $[Tc(CO)_3]^+$, preferably $(TcO)^{3+}$.

In particular $X_5$ comprises Norleucine.

In particular $X_1$ is selected from the group comprising: Threonine, Serine, Tyrosine, Aspartic acid, Glutamic acid.

In particular $X_2$ is Glycine.

In particular the peptide tag is selected from the group consisting of:

(SEQ ID NO: 14); (SEQ ID NO: 15); SEQ ID NO: 16); (SEQ ID NO: 17); (SEQ ID NO: 18); (SEQ ID NO: 19); (SEQ ID NO: 20); (SEQ ID NO: 21); (SEQ ID NO: 22); (SEQ ID NO: 23); (SEQ ID NO: 24); (SEQ ID NO: 25); (SEQ ID NO: 26); (SEQ ID NO: 27); (SEQ ID NO: 34); (SEQ ID NO: 39); (SEQ ID NO: 2); (SEQ ID NO: 3); (SEQ ID NO: 4); (SEQ ID NO: 5); (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13).

According to an eighth aspect of the present invention there is provided a method of labelling with a Tc core, a protein of interest which comprises a peptide tag according to an earlier aspect of the present invention, comprising the steps of:

a) the successive addition to an aqueous solution containing said protein of interest, of:
   (i) an aqueous solution of a reducing agent under basic pH conditions;
   (ii) an aqueous solution of a salt of technetic (VII) acid (pertechnetate salt);

b) incubation of the solution from step a) for between 1 to 10 minutes at room temperature.

Preferably, the aqueous solution of a reducing agent is $SnCl_2$.

Preferably, said pertechnetate salt is sodium, potassium or lithium salt.

The Inventors have shown that proteins of interest comprising one of the chelating peptide tags they have developed, can be labelled using several protocols with a Tc core. They have also shown that such labelled proteins of interest are stably labelled Preferably during step a) (iii) an aqueous solution of ammonium salt of technetic (VII) acid (ammonium pertechnetate or $NH_4TcO_4$) is also added.

For a better understanding of the invention and to show how the same may be carried into effect, there will now be shown by way of example only, specific embodiments, methods and processes according to the present invention with reference to the accompanying drawings in which:

FIG. 1: Direct $[TcO]^{3+}$ labelling of UBI 29-41: the UV absorbance is shown in continuous line and the radioactivity in dotted line, using the $^{(99m+g)}Tc$ from the $^{99m}Tc/^{99}Mo$ generator (A) and $^{99g}Tc$ from $[NH_4^{99}TcO_4]+^{(99m+g)}TC$ from the $^{99m}Tc/^{99}Mo$ generator (B).

Figure 2:
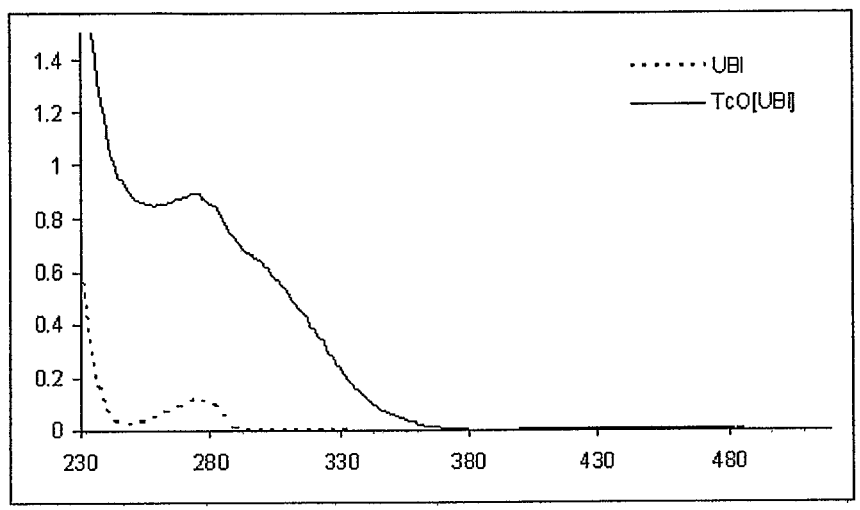

FIG. 2: Absorbance spectrum at 220 nm of UBI 29-41 in free form (dotted line) and in complex with $[TcO]^{3+}$ (continuous line).

FIG. 3: Schematic Representation of a) RC-121 (SEQ ID NO: 40) and b) TGRRRGG-RC-121 (SEQ ID NO: 41).

Figure 4:
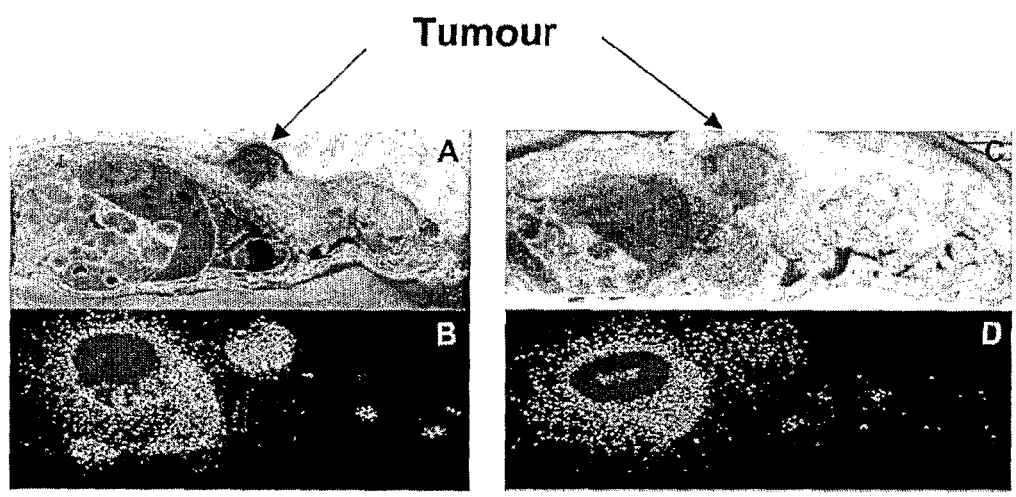

FIG. 4: Whole body sections of AR4-2J xenografted mice 4 hours post injection after: 1 μg of $TcO[_HTGRRRGG-RC-121$ (SEQ ID NO: 41)] (134 μCi) (A, B) and co-injection of 1 μg $_H$TGRRRGG-RC-121 (SEQ ID NO: 41)] (134 μCi) and 125 μg of RC-121 (C, D). A and C are the pictures of the sections and B and D represents the detection of the β-emission of the $^{99m}Tc$ (15 Key) produced with a β-imager (BIO-SPACE inc.).

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

DEFINITIONS

Amino acid residues in a polypeptide sequence are designated herein according to the one-letter code, in which, for example, Q means Gln or Glutamine residue, R means Arg or Arginine residue and D means Asp or Aspartic acid residue.

Chelated peptide tag refers to a short peptide sequence which has chelated a Tc or Re core and is chemically linked thereto.

N3O chelating sequence, refers to a sequence which chelates the TcO core via three nitrogen atoms and one oxygen atom. Likewise a N4 chelating sequence refers to once which chelates the TcO core via four nitrogen atoms.

Native residue, refers to the amino acid residue present in the specified peptide sequence prior its replacement by another natural or non-natural amino acid.

Non-natural/natural amino acid residues, natural amino acid residues are those found in vivo and which are produced by at least one naturally occurring organism, although they can also be produced by various chemical means. Non-natural amino acid residues do not occur in vivo and can only be produced by various chemical means.

Peptide linker, refers to a string of several amino acid residues which are not expected to affect either the native or new functional domains. Examples include a series of six Histidine residues or two Glycine residues, but many other linkers are known in the art of various lengths and amino acid composition.

Peptide tag, refers to a short peptide sequence which is able to chelate a Tc or Re core.

Tc or Re core, refers to a Tc or Re atom which has been chemically reduced into an active form. Examples of a Tc core include the diatomic Tc(V) core $[TcO]^{3+}$ or the Tc(I) triscarbonyl $[Tc(CO)_3]^+$.

TcO, when in complex with the described chelating peptide tag sequences, the Tc core may be called TcO, in the format TcO[peptide] or TcO-peptide.

Side chain refers to the chemical group of an amino acid which differs between different naturally occurring amino acid residues, for instance in Glycine it is a H— and in Alanine a $CH_3$—. A natural or non-natural amino acid lacking the side chain of another residue is one in which the relevant side chain is missing for instance Tyrosine comprises a side chain which consists of a cyclic hydrocarbon with an OH group, whereas the related amino acid Phenylalanine does not comprise an OH group and hence can be used to replace Tyrosine as an amino acid lacking the side chain of the native (Tyrosine) residue.

SPECT means Single photon emission computed tomography which is a nuclear medicine tomographic imaging technique using gamma rays. It is very similar to conventional nuclear medicine planar imaging using a gamma camera. However, it is able to provide 3D information. This information is typically presented as cross-sectional slices through the patient, but can be freely reformatted or manipulated as required.

"syn/anti isomers"—In the commonly used zig-zag drawings substituents may lie on the same side of the carbon chain, a syn orientation, or on opposite sides, an anti orientation.

Example 1

Material and Methods

Fluorenylmethyloxycarbonyl (Fmoc) amino acids (Nova Biochem, Laufelfingen, Switzerland) were used with the following side chain protecting groups: tert-butyl ether for Ser and Thr; tert-butyl ester for Asp and Glu; 2,2,5,7,8-pentamethylchromane-6-sulfonyl for Arg; trityl for Cys, Gln and Asn; and tert-butyloxycarbonyl for Lys. Solvents and reagents for peptide synthesis were from SDS (Peypin, France) or Fluka (St. Quentin Fallavier, France).

Ammonium pertechnetate ($NH_4TcO_4$) was purchased from the National Oak Ridge Laboratory (USA) and reoxydized using a published procedure (37). The concentration of the aqueous solution used in the labeling experiment were determined using electronic absorption spectroscopy assuming a 6220 $M^{-1}$ $cm^{-1}$ extinction coefficient for pure pertechnetate at 244 nm.

Analysis of the labeling reaction mixture were made using a Varian Prostar HPLC system equipped with a Prostar 335 Photodiode array detector (Varian, Les Ulis, France) and a Berthold HERM LB500 γ-detector (Berthold, Thoiry, France).

1.1 Peptide Synthesis.

Designed peptides were obtained by solid phase synthesis on an automatic peptide synthesizer (model 433A, Applied Biosystems, Foster City, USA) by using fluorenylmethyloxycarbonyl (Fmoc)-amino acid derivatives, Novasyn TGR (Nova Biochem, France) and N-hydroxy-benzotriazole (HOBt)/N,N'-dicyclohexylcarbodiimide (DCCI, Applied Biosystems) mediated coupling. Peptide synthesis was accomplished on a 0.10 mmol scale, with single 30 min coupling and 10-fold Fmoc-amino acid excess (1 mmole), followed by capping with acetic anhydride. After completion of synthesis, the peptide was cleaved from the resin with simultaneous removal of side-chain protecting groups by treatment with a mixture of 95% trifluoroacetic acid, 2.5% water, 2.5% triisopropylsilane for 2 h at room temperature for the 13-mer peptides and 30 minutes for shorter peptides. For the 13-mers, the resin was then filtered and the free peptide precipitated in methyl-tert-butyl ether at 4° C. After centrifugation and washing three times with ether, the peptide was dissolved in 20% acetic acid and lyophilized. For shorter peptides, the solvent was removed in vacuo and the resulting yellow oil was dissolved in 20% acetic acid and lyophilized. The reduced peptides were purified by preparative reversed-phase high pressure liquid chromatography (HPLC) using non-linear gradient of eluent B (0.09% trifluoroacetic acid, 90% acetonitrile in water) in eluent A (0.1% trifluoroacetic acid in water) over 80 min, on a Supelco BioWide Pore C18 column (10×250 mm) at 4.5 mL/min flow rate. Peaks were analyzed in analytical HPLC and >95% pure fractions were pooled and lyophilized.

1.2 Peptide Sequence Analysis.

Amino acid sequence analysis was performed with automated Edman degradation using an ABI Model 492 Procise Protein Sequencing System (Applied Biosystems).

1.3 Labeling Procedure and HPLC Analysis.

In a typical experiment, to 15 $_1$ μl of a 580 μM aqueous solution of the peptide were added 5 μl of a 1 mg/ml solution of $SnCl_2$ in water followed by 10 μl of a 0.1N NaOH solution and 2.5 μl of a freshly prepared 5.5 mM aqueous solution of $NH_4TcO_4$. The reaction mixture was incubated at room temperature for 5 minutes. 50 μl of a 0.1 mg/ml solution of caffeine in 0.05% trifluoroacetic acid in water used as a quantification standard were added. The solution was acidified with 0.8 µl of IN HCl and diluted to 120 µl with eluent A (0.05% trifluoroacetic acid in water; final pH 2.5). The mixture was analyzed using a Grace Altima C8 column (Grace Davison, Lokeren, Belgium) and an optimized non linear gradient of eluent B (0.045% trifluoroacetic acid, 90% acetonitrile in water) into eluent A.

In the case of BPTI (SEQ ID NO: 32) and its variant TGRRRGG-BPTI (SEQ ID NO: 33) which includes the TGRRR peptide tag (SEQ ID NO: 22) and a peptide linker GG (SEQ ID NO: 36), similar conditions as described in protocol 2 (see example 2), were applied except that 50 µg of the proteins were use for the $[TcO]^{3+}$ labeling experiments.

For each peptide, the labeling yield was calculated using internal calibration. A first experiment was carried out under the conditions reported above and the area of the peak corresponding to the unreacted peptide was normalized to that of the peak corresponding to the internal reference caffeine giving the ratio $R_1$. A second experiment was carried out under the same conditions excepted that $TcO_4^-$ was not added to the reaction mixture. The peak corresponding to the unreacted peptide was normalized to that of caffeine to give the ratio $R_2$. The labeling yield was calculated as $(1-R_1/R_2)$.

1.4 Cysteine Challenge.

A solution containing 16 µg of lyophilized TcO[UBI 29-41] (SEQ ID NO: 1) was added to 32 µl of Cysteine solution in PBS pH 7.4. Three concentrations of Cysteine solution were used: 100 mM, 15 mM and 1 mM corresponding respectively to a molar ratio Cysteine:Tc-UBI-WT of 333, 53 and 3. The samples were incubated for 20 h at 310 K prior to HPLC and ESI-MS analysis. Similar experiment was performed for TcO[TGRRR] (SEQ ID: NO 22) complex. 13 µg of lyophilized TGRRR(SEQ ID: NO 22)-TcO complex were added to 64 µl of 15 mM Cysteine solution in PBS pH 7.4 corresponding to a TcO[TGRRR] (SEQ ID: NO 22): Cysteine molar ratio of 50. This solution was incubated for 20 h at room temperature prior to HPLC analysis.

1.5 Large-Scale Purification and Isolation of TcO[Peptide] Complex.

To 1 mg of UBI 29-41 (SEQ ID NO: 1) in 1 ml of water were added 333 µl of a 1 mg/ml $SnCl_2$ solution in water, 667 µl of 0.1N NaOH and 133 µl of a freshly prepared aqueous solution of ammonium pertechnetate. The reaction mixture was incubated for 5 minutes at room temperature. It was diluted with 9 ml of a 50 mM aqueous ammonium trifluoroacetate solution before HPLC injection. The technetium complex was purified on a 4.6×150 mm Altima C8 column using a linear gradient of 20% to 80% of eluent B (50 mM ammonium trifluoroacetate in 70% aqueous methanolic solution) into eluent A (50 mM ammonium trifluoroacetate) over a period of 40 minutes.

1.6 Mass Spectrometry Analysis.

LC-MS analyses were performed on a HPLC Agilent 1100 Series coupled on-line to an ESI-Ion Trap mass spectrometer Esquire HCT (Bruker-Daltonics, Germany). Elution was carried out on a Grace Altima C8 column (Grace Davison, Lokeren, Belgium) at a flow rate of 600 µL/min with a linear gradient of eluent B (0.045% trifluoroacetic acid, 90% acetonitrile in water) into eluent A (0.05% trifluoroacetic acid in water). By use of a splitting system 90% of the elution from the column was directed to the DAD (Diode-Array Detector) detector for UV absorbance measurement.

The remaining 10% of the elution from the column was directed to the ESI-MS for MS acquisition. Nitrogen served as the drying and nebulizing gas, while helium gas was introduced into the ion trap for efficient trapping and cooling of the ions generated by the ESI as well as for fragmentation processes. Ionization and mass analyses conditions (capillary high voltage, skimmer and capillary exit voltages and ions transfer parameters) were tuned for an optimal detection of compounds.

1.7 NMR Experiments.

The UBI-29-41 peptide (SEQ ID NO: 1) and the purified TcO complex were prepared at 1.5 mM in 600 µl 90% $H_2O$/10% $D_2O$. The pH was adjusted to 5.8 for both samples. $^1H$ chemical shift were measured using internal reference 3-(trimethylsilyl)[2,2,3,3,-2H4]propionate (TSP).

Backbone and side chain assignment experiments were performed at 295 K for UBI-29-41 (SEQ ID NO: 1) and its TcO complex on a Bruker DRX-700 spectrometer equipped with a 5 mm triple resonance cryoprobe.

The NMR experiments performed to assign the side chain and backbone resonances of TGRRR (SEQ ID NO: 22) and its TcO complex were recorded on a Bruker DRX-500 equipped with 5 mm BBI Z gradients probe in 90% $H_2O$/10% $D_2O$ and 100% $D_2O$.

A series of $^1H$-$^1H$ and $^1H$-$^{13}C$ 2D experiments were recorded. $^1H$-$^1H$ total correlated spectroscopy (TOCSY) was recorded with a 80 ms mixing time with a DIPSI2 sequence for mixing and water suppression with a 3-9-19 pulse sequence with gradients. 2D off resonance ROESY spectrum (TROESY) was recorded with a 100 ms ROESY spin lock time.

2D $^1H$-$^{13}C$ HSQC-TOCSY experiment were recorded with correlation via double inept transfer using sensitivity improvement and DIPSI2 sequence for homonuclear Hartman-Hahn mixing. The spectra were processed with the Topspin Bruker software and analyzed with the program SPARKY.

1.8 Rat Cell Culture

Rat pancreatic carcinoma AR4-2J cells expressing predominantly the Somatostatin receptor subtype 2 (SST-2) were used for in vivo evaluation of the $^{99m}$TcO labelled somatostatin analog. The cells were grown in tissue culture dishes (Falcon) which were incubated at 37° C. in an atmosphere of 5% $CO_2$ and 95% humidified air in DMEM medium with 4.5 g/l glucose supplemented with 1% L-glutamine, 20% foetal calf serum, 1% penicillin/streptomycin and amphotericin B (1 µg/mL). Subculturing was performed with a trypsin/EDTA (0.05%/0.02% w/v) solution. All products were purchased from Sigma (Saint-Quentin Fallavier; France). At 100% confluence, the medium was removed and the cells were harvested using Versen buffer (PBS+5 mM EDTA), washed with ice-cold phosphate buffer and finally centrifuged at 1000 g for 7 min (4° C.). The pellet was suspended in ice-cold buffer (10 mM $MgCl_2$, 0.25% BSA, 50 mM HEPES pH7.5, 1% protease inhibitor cocktail (Sigma) and cells suspension was stored in ice before binding experiments.

1.9 [$^{125}$I]-[Tyr$^1$]-Somatostatin Binding Assays

All binding experiments for AR4-2J cells were done at 37° C. in 10 mM $MgCl_2$, 0.25% BSA, 50 mM HEPES pH7.5, 1% protease inhibitor cocktail (Sigma). The density of AR4-2J cells suspension was checked before every binding assay and adjusted so that no more than 10% of proposed radio-ligand was specifically bound (typically around 3000 cpm). Similar experiments were performed to determinate the effect of increasing concentrations of RC-121 (SEQ ID NO: 40), $_H$TGRRRGG-RC-121 (SEQ ID NO: 41) and TcO[$_H$T-GRRRGG-RC-121] (SEQ ID NO: 41) on the equilibrium binding of [$^{125}$I]-[Tyr$^1$]-somatostatin with AR4-2J cells suspension expressing SST-2. Typically, 0.5 nM [$^{125}$I]-[Tyr$^1$]-somatostatin as tracer was incubated with 15 µl cells suspension, for 45 min in a final assay volume of 100 µl. Non-specific binding was determined in the presence of 5 µM somatostatin-28. Incubation was terminated by addition of ice-cold washing buffer (Tris 10 mM pH7.2) and rapid filtration over Whatman GF/C glass fiber filters pre-soaked in 0.5% polyethylenimine. The filters activity was measured in a Cobra gamma counter. Each experiment has been performed in duplicates at least two times.

1.10 Binding Data Analysis

The competition binding curves from individual experiments (n≥2) were analyzed by nonlinear regression analysis using Kaleidagraph 4.0 (Synergy Software, Reading, Pa.).

After subtraction of the non-specific binding and normalization, data obtained with $[^{125}I][Tyr^1]$-somatostatin were analyzed using the Hill equation to estimate the $IC_{50}$ values. The affinities of peptides in inhibiting the binding of $[^{125}I]$-$[Tyr^1]$-somatostatin, expressed as $pK_i$, were calculated from the $IC_{50}$ values by applying the Cheng-Prussoff correction (Kd for SST-2=1 nM).

1.11 Biodistribution and Imaging Studies in Mice.

Females Balb/c nude mice weighing 20 g were purchased from Charles River Laboratories (L'Arbresle, France). The mice were kept in a conventional animal facility and had access ad libitum to food and drink. The experimental protocol has been approved by the local ethical committee for animal experimentation.

Mice were implanted subcutaneously with 5-6 millions AR4-2J cells freshly suspended in sterile PBS. Thirteen days after inoculation, the mice showed solid palpable tumour masses. At this time, mice were injected in the tail vein with about 1 μg of $^{99(m+g)}$TcO-labelled compound corresponding to 150-250 μCi. After 1 h, 4 h or 24 h time period, the mice were sacrificed by ex-sanguination under anaesthesia. Organs of interest, blood and urine were collected and weighted. The radioactivity was measured with a gamma counter. The evaluated compounds were TcO[$_H$TGRRRGG-RC-121] (SEQ ID NO: 41) and TcO[$_H$TGRRR] (SEQ ID NO: 27). A block control experiment was achieved by simultaneously injecting the TcO[$_H$TGRRRGG-RC-121] (SEQ ID NO: 41) complex with a 125 fold excess of the reference compound RC-121.

1.12 Imaging

Full Body section analysis: the mice were injected by caudal vein and sacrificed 4 hours later. For imaging, the mice were anesthesied and then immersed in an −80° C. mixture of dry ice and isopentane to prevent CNT tissue redistribution. After blocking the body in mounting medium, tissue sections (20 μm) were made at −20° C. with a slicing microtome (LEICA Microsystems, France). Sections were kept at room temperature for 2 hours in the presence of silica gel to ensure complete drying.

The quantitative determination of the radioactivity in dried tissue sections and imaging were carried out using a β-imager (Biospace Lab, Paris, France).

Example 2

Results 2.1 Synthesis, Radiolabeling and Characterization of $^{99m+g}$Tc UBI 29-41.

Two different protocols were used to label the peptide UBI 29-41 (SEQ ID NO: 1) and characterize its complex. Protocol 1 was adapted from that reported by Melendez-Alafort et al. for the direct labelling of UBI 29-41 (SEQ ID NO: 1) using a commercially available pertechnetate solution eluted from a $^{99}$Mo/$^{99m}$Tc generator (19).

In protocol 1, 5 μl of 1 mg/ml SnCl$_2$ solution in water prepared extemporaneously, 10 μl of NaOH 0.1N solution, 2.4 μl of 100 nM $^{99(m+g)}$TcO$_4^-$ in saline solution were successively added to 15 μl of 1 mg/ml aqueous solution of UBI 29-41 (SEQ ID: NO 1) in water. The final concentrations of UBI 29-41 (SEQ ID: NO 1), SnCl$_2$, $^{99(m+g)}$TcO$_4^-$ were respectively 270 μM, 840 μM and 7.4 nM. The pH of the solution was 10.5.

The reaction was left for 5 min at room temperature. The resulting products were characterized by reverse-phase HPLC. The inventors preferred method to characterize the complexes formed during the labelling of the peptide UBI 29-41 (SEQ ID: NO 1) is ESI-MS. In order to ensure that the acidic conditions compatible with this technique do not lead to de-coordination of the complex, three elution conditions were used at pH 2.5, 5.5 and 6.8. No significant differences were observed between these three conditions.

FIG. 1A shows the superimposition of the UV chromatogram (at 220 nm) and γ-radio-chromatogram of the labelling solution with elution at pH 2.5. The γ-radio-chromatogram demonstrates the presence of a product eluting at a higher retention time than the main species giving the most important absorption at 220 nm. However, the reaction conditions used in protocol 1 did not permit the inventors to obtain a significant amount of the Tc[UBI 29-41] (SEQ ID: NO 1) complex precluding characterization of the products by ESI-MS. This is mainly due to the limited Tc concentrations delivered by the $^{99}$Mo/$^{99m}$Tc generator.

In order to increase the labelling yield to characterize the products of the Tc labelling experiment, the inventors designed a second labelling protocol, protocol 2. 5 μl of 1 mg/ml SnCl$_2$ solution in water prepared extemporaneously, 10 μl of NaOH 0.1N solution, 2.4 μl of 100 nM $^{99(m+g)}$TcO$_4^-$ in saline solution and 2.4 μl of a 5.5 mM solution of [NH$_4$$^{99g}$TcO$_4$] were successively added to 15 μl of 1 mg/ml aqueous solution of UBI 29-41 (SEQ ID: NO 1) in water. The final concentrations of UBI 29-41 (SEQ ID: NO 1), SnCl$_2$ and $^{99}$Tc were respectively 270 μM, 840 μM and 407 μM. The reaction mixture was left 5 minutes at room temperature.

The characterization of the products of the Tc labelling experiment with protocol 2 was achieved by LC-positive ion ESI-MS analysis. As illustrated in FIG. 1B, HPLC UV and radio-profiles displayed one most abundant peak at the same retention time. LC-positive ion-ESI-MS characterization of this most abundant peak was in good agreement with the formation of a TcO[UBI 29-41] monoadduct (m/z of 1845.6 Da). This mass might correspond to 1733.5 Da (UBI 29-41)+ 115 Da (TcO$^{3+}$)−3 Da (3H$^+$). This matched the mass found within the margin of error of the experiments. Moreover the electronic absorption spectra of the monoadduct exhibited a large absorption centred at 274 nm (FIG. 2) not observed in the absorption spectra of UBI 29-41 (SEQ ID: NO 1). This absorption might correspond to a ligand to metal charge transfer (LMCT) band ($\epsilon$=8887 mol$^{-1}$·l·cm$^{-1}$).

The TcO labelling yield of UBI 29-41 (SEQ ID: NO 1) with protocol 2 was determined using a calibration procedure described in Material and Methods. This allowed an accurate determination of the TcO labelling yield that is reported in Table I for UBI 29-41. It must be noted that, in the experimental conditions of protocol 2, the labelling yield of UBI 29-41 (SEQ ID: NO 1) was 79%.

2.2 Identification of the Sidechains Playing a Role in TcO$^{3+}$ Chelation.

In order to identify the location of the TcO$^{3+}$ chelation site in UBI 29-41 (SEQ ID: NO 1), the inventors synthesized 11 analogs of this peptide (Table I). Each of these analogs corresponded to the replacement of one sidechain present in this fragment of Ubiquicidine by a non-natural or natural amino acid where the functional group of the native residue is removed. Arginine residues were replaced by Norvaline (Nva) residues, Threonine, Glutamic acid and Asparagine residues were replaced by Amino butyric acid (Abu) residues, Lysine and Methionine residues by Norleucine (Nle) residues and Tyrosine by Phenylalanine. Alanine and Glycine residues were not replaced.

The 11 analogs of UBI 29-41 (SEQ ID: NO 1) are hereafter designated as UBI-A1 to UBI-A11 (Table I).

vations suggested that, none of the chemical functions suppressed in these different analogs were directly involved in the chelation of the $[TcO]^{3+}$ core.

In order to determine the precise location of the $[TcO]^{3+}$ chelation site in UBI 29-41 (SEQ ID: NO 1) and the coordinating functions, the inventors analyzed the TcO[UBI 29-41]

TABLE I

Characterization of the $^{99(m+g)}$Tc labelling products of the analogs of UBI 2941 (UBI-WT).

| SEQ ID NO: | | | | | | | | Peptide Sequence | | | | | | | |
|---|---|---|---|---|---|---|---|---|---|---|---|---|---|---|---|
| 1 | UBI-WT | Ac— | T | G | R | A | K | R | R | M | Q | Y | N | R | R | NH2 |
| 2 | UBI-A1 | Ac— | Abu | G | R | A | K | R | R | M | Q | Y | N | R | R | NH2 |
| 3 | UBI-A2 | Ac— | T | G | Nva | A | K | R | R | M | Q | Y | N | R | R | NH2 |
| 4 | UBI-A3 | Ac— | T | G | R | A | Nle | R | R | M | Q | Y | N | R | R | NH2 |
| 5 | UBI-A4 | Ac— | T | G | R | A | K | Nva | R | M | Q | Y | N | R | R | NH2 |
| 6 | UBI-A5 | Ac— | T | G | R | A | K | R | Nva | M | Q | Y | N | R | R | NH2 |
| 7 | UBI-A6 | Ac— | T | G | R | A | K | R | R | Nle | Q | Y | N | R | R | NH2 |
| 8 | UBI-A7 | Ac— | T | G | R | A | K | R | R | M | Abu | Y | N | R | R | NH2 |
| 9 | UBI-A8 | Ac— | T | G | R | A | K | R | R | M | Q | F | N | R | R | NH2 |
| 10 | UBI-A9 | Ac— | T | G | R | A | K | R | R | M | Q | Y | Abu | R | R | NH2 |
| 11 | UBI-A10 | Ac— | T | G | R | A | K | R | R | M | Q | Y | N | Nva | R | NH2 |
| 12 | UBI-A11 | Ac— | T | G | R | A | K | R | R | M | Q | Y | N | R | Nva | NH2 |
| 13 | H-UBI | H— | T | G | R | A | K | R | R | M | Q | Y | N | R | R | CO2 |

| SEQ ID NO: | Labelling Yield | ESI-MS (peptide) | ESI-MS (Complex) |
|---|---|---|---|
| 1 | 79 | 1733.5 | 1845.6 |
| 2 | 34 | 1717 | n.d. |
| 3 | 78 | 1676.7 | 1788.6 |
| 4 | 86 | 1718.5 | 1830.6 |
| 5 | 87 | 1676.4 | 1788.6 |
| 6 | 84 | 1676.6 | 1788.5 |
| 7 | 92 | 1715.5 | 1828 |
| 8 | 88 | 1690.5 | 1802.2 |
| 9 | 92 | 1717.9 | 1829.5 |
| 10 | 91 | 1704.4 | 1816.6 |
| 11 | 95 | 1676.7 | 1788.2 |
| 12 | 93 | 1676.8 | 1788.5 |
| 13 | >95 | 1692.3 | 1804.23 |

$^{a}$The labelling Yield was calculated as (1-R1/R2), were R1 corresponds to the ratio of the unreacted peptide on that of the internal reference caffeine in the $^{99(m+g)}$Tc labelling experiment under conditions of protocol 2 and R2, the ratio of the unreacted peptide on that of the internal reference caffeine in the conditions of protocol 2 but without $TcO_4^-$. Taken into account the uncertainty on the integration of the HPLC peaks, the Inventors assume an uncertainty below 10% on the calculated labelling yields.

These analogs were labelled using protocol 2 and the products were characterized by HPLC and ESI-MS. Only one analog displayed a significant variation in the labelling yield as compared to the parent peptide UBI 29-41 (SEQ ID: NO 1). The analog UBI-A1 corresponded to the substitution of the residue $T_1$ by an aminobutyric acid residue. This result suggested that the OH group of T1 might be one of the TcO chelating functions. Analog UBI-A2 gave a similar labelling yield as UBI 29-41 suggesting that R2 was not involved in the chelation of TcO. Analogs UBI-A3 to UBI-A11 displayed $[TcO]^{3+}$ labelling yields in the range 84-95%. These observations suggested that, none of the chemical functions suppressed complex and the free peptide by $^1H$ and $^{13}C$ NMR spectroscopy in water solution at pH 5.8. In the free peptide as well as in the TcO-peptide complex, only one set of resonances was observed in the NMR experiment suggesting that only one conformation was present in solution or that one conformation is predominant.

The $^1H$ and $^{13}C$ assignment of the UBI 29-41 (SEQ ID NO: 1) and the TcO[UBI 29-41] peptide are reported in Table II and III.

$^1H$ and $^{13}C$ resonances of residues $R_7$, $R_{12}$ and $R_{13}$ in the case of the Tc free UBI 29-41 and of residues $R_6$, $R_7$, $R_{12}$ and $R_{13}$ in TcO-UBI 29-41 complex could not be assigned due to coincidence of the $^1H$ and $^{13}C$ resonances. However the characteristic pattern of the other residues in the HSQC-TOCSY experiments in conjunction with the TROESY and TOCSY experiments allowed to assign unambiguously the NH, Hα, Hβ, Hγ, Hε, Hε, Cα, Cβ, Cγ, Cδ and Cε resonances of all other residues in the case of the UBI 29-41 (SEQ ID: NO 1) and the TcO[UBI 29-41] complex.

TABLE II $^1H$ and $^{13}C$ (in parentheses) NMR chemical shift assignments[a] of UBI 29-41.

| | HN | αCH | βCH | Others |
|---|---|---|---|---|
| $T_1$ | 8.28 | 4.26(62.80) | n.d.[b](70.19) | γCH$_3$: 1.24(21.97); N-terminal CH$_3$: 2.04(20.04) |
| $G_2$ | 8.57 | 3.97(46.03) | | |
| $R_3$ | 8.35 | 4.30(56.62) | 1.77/1.87(31.17) | γ: 1.64(27.56); δ: 3.21(43.80) |
| $A_4$ | 8.25 | 4.29(53.02) | 1.40(19.56) | |
| $K_5$ | 8.27 | 4.27(56.80) | 1.43/1.49(33.38) | γ: 1.70/1.76(25.29); δ: 1.84(29.51); ε: 3.01(42.57) |
| $R_6$ | n.d. | n.d. | n.d. | |
| $R_7$ | n.d. | n.d. | n.d. | |
| $M_8$ | 8.43 | (52.80) | 1.97(33.27) | γ: 2.50(32.39); ε: 1.19(20.04) |
| $Q_9$ | 8.35 | 4.31(56.09) | 1.93/2.01(30.13) | γ: 2.28(34.14) |
| $Y_{10}$ | 8.30 | 4.57(58.25) | 2.91/3.05(39.33) | |
| $N_{11}$ | 8.41 | 4.69(53.37) | 2.71/2.80(39.41) | |
| $R_{12}$ | n.d. | n.d. | n.d. | |
| $R_{13}$ | n.d. | n.d. | n.d. | |

[a]Chemical shift were reference relative to TSP and were measured at 295K. $R_6$, $R_7$, $R_{12}$ and $R_{13}$ $^1H$ and $^{13}C$ resonances were not assigned due to complete overlap of the signals.
[b]$^1H$ chemical shift could not be assigned due to overlapping resonance with the residual HDO signal in the $^1H$—$^{13}C$ HSQC-TOCSY experiment.

TABLE III $^1H$ and $^{13}C$ (in parentheses) NMR chemical shift assignments of the TcO[UBI 29-41] complex (UBI-WT).

| | HN | αCH | βCH | Others |
|---|---|---|---|---|
| $T_1$ | 8.19 | 4.74(63.29) | 5.02(79.48) | γCH$_3$: 0.864(20.64); N-Terminal CH$_3$: 2.09(17.41) |
| $G_2$ | — | 3.31/3.96(46.43) | | |
| $R_3$ | — | 4.71(67.34) | 1.99/2.16(33.66) | γ: 1.59/1.79(26.13); δ: 3.19(44.22) |
| $A_4$ | — | 4.29(57.56) | 1.58(19.89) | |
| $K_5$ | 7.51 | 4.35(56.50) | 1.69(33.85) | γ: 1.38(25.27); δ: 1.85(29.59); ε: 2.91(42.60) |
| $R_6$ | 8.31 | 4.32(56.79) | 1.90/1.79(31.14) | γ: 1.64(27.61); δ: 3.22(43.81) |
| $R_7$ | n.d. | n.d. | n.d. | n.d. |
| $M_8$ | 8.37 | 4.45(55.93) | 1.99(33.16) | γ: 2.53(32.43); ε: 1.19(19.98) |
| $Q_9$ | 8.31 | 4.31(56.22) | 1.93/2.00(30.02) | γ: 2.27(34.14) |
| $Y_{10}$ | 8.26 | 4.57(58.28) | 2.93/3.06(39.26) | |
| $N_{11}$ | 8.38 | 4.68(53.42) | 2.72/2.81(39.28) | |
| $R_{12}$ | n.d. | n.d. | n.d. | n.d. |
| $R_{13}$ | n.d. | n.d. | n.d. | n.d. |

[a]Chemical shift were reference relative to TSP and were measured at 295K. $R_7$, $R_{12}$ and $R_{13}$ $^1H$ and $^{13}C$ resonances were not assigned due to complete overlap of the signals.

The first observation that may give information on the location of the coordination site of [TcO]$^{3+}$ concerns the absence, in the TOCSY spectrum as well as in the HSQC-TOCSY experiment, of correlations between amide protons and the corresponding sidechain protons of residue $G_2$, $R_3$ and $A_4$ of TcO[UBI 29-41]. This suggests that these three protons were lost upon the formation of the TcO core.

Comparison of the and $^{13}C$ chemical shifts of the two samples revealed other interesting features. The Cα resonances of residue $R_3$ and $A_4$ displayed important downfield shift respectively by 10.72 and 4.54 ppm. In addition, the Cβ resonance of residue $T_1$ displayed a downfield shift by 9.29 ppm. Other significant chemical shift changes between the free peptide and its [TcO]$^{3+}$ complex were observed. The Hα resonance of residue $T_1$ displayed a shift by 0.48 ppm while the γCH3 of this residue displayed an upfield shift by 0.376 ppm upon TcO complexation.

In addition, the $^1H$ resonances of the two samples showed that the Hα1 and Hα2 protons resonances of residue $G_2$ that overlapped likely due to conformational averaging in the NMR timescale in the free peptide, displayed a chemical shift difference by about 0.6 ppm in the TcO[UBI 29-41] complex. This suggests that, upon complexation with the [TcO]$^{3+}$ core, the peptide adopts a defined structure in the region of $G_2$ leading to a different magnetic environment for the two Ha protons. One additional observation regarding the $^1H$ chemical shift change between UBI 29-41 (SEQ ID NO: 1 and its [TcO]$^{3+}$ complex concerns the HN resonance of residue $K_5$. Even this HN proton was still present in the TcO[UBI 29-41] complex, it displayed an important upfield chemical shift change by 0.76 ppm indicating that its magnetic environment had been significantly modified upon complexation of the [TcO]$^{3+}$ core.

Overall, these observations suggest that the [TcO]$^{3+}$ chelation site in UBI 29-41 is located at the N-terminal side of the peptide and involves residues $T_1$, $G_2$, $R_3$ and $A_4$. Residue $G_2$, $R_3$ and $A_4$ might coordinate the [TcO]$^{3+}$ core by their amide nitrogens that were lost upon complex formation of the [TcO]$^{3+}$ core.

2.3 Short Effective [TcO]$^{3+}$ Chelating Peptide Sequences Derived from UBI 29-41 (SEQ ID NO: 1).

The results, described above, regarding the [TcO]$^{3+}$ chelating capacity of the UBI 29-41 (SEQ ID: NO 1) and of its analogs in conjunction with the NMR analysis of the TcO [UBI 29-41] complex allowed the inventors to locate the chelation site in the N-terminal position of UBI 29-41. This led the inventors to synthesize the minimal sequence TGRA (SEQ ID NO: 14) to evaluate its intrinsic [TcO]$^{3+}$ chelation capacity according to protocol 2. The labelling yield determined for this peptide sequence was 11% (Table IV). This result suggest that, in the experimental conditions of protocol 2, even if a small fraction of the TGRA (SEQ ID NO: 14) peptide chelate the [TcO]$^{3+}$ core, other important determinants of the TcO chelation in UBI 29-41 are lacking in the TGRA (SEQ ID NO: 14).

This result as compared to the parent peptide UBI 29-41 (SEQ ID NO: 1) prompted the inventors to synthesize a series of peptides to investigate in detail the determinants of the [TcO]$^{3+}$ chelation efficiency in this sequence. The sequence of these peptides and their labelling yields are reported in Table IV. The ESI-MS analysis demonstrated that the complexes obtained correspond in all case to monoadducts of [TcO]$^{3+}$ with the abstraction of 3 H$^+$.

TABLE IV

Characterization of the $^{99(m+g)}$Tc labelling products of the UBI-29-41 fragments and their analogs.

| | SEQ ID NO: | Peptide Sequence | | | | | | Labelling Yield [a] | ESI-MS (peptide) | ESI-MS (Complex) |
|---|---|---|---|---|---|---|---|---|---|---|
| P1 | 14 | Ac | T G R A | NH2 | | | | 11 | 444.3 | 556.1 |
| P2 | 15 | Ac | T G R A | K | NH2 | | | 40 | 572.5 | 684.2 |
| P3 | 16 | Ac | T G R A | K | R | NH2 | | 67 | 728.5 | 840.3 |
| P4 | 17 | Ac | T G R A | K | R | R | NH2 | 71 | 884.6 | 996.5 |
| P5 | 18 | Ac | T G R A | K | R | Nva | NH2 | 63 | 827.6 | 939.5 |
| P6 | 19 | Ac | T G R A | R | R | NH2 | | 86 | 756.6 | 868.4 |
| P7 | 20 | Ac | T G R A | A | R | NH2 | | 19 | 671.4 | 783.2 |
| P8 | 21 | Ac | T G R R | NH2 | | | | 43 | 529.3 | 641.3 |
| P9 | 22 | Ac | T G R R | R | NH2 | | | 68 | 685.4 | 797.4 |
| P10 | 23 | Ac | T G G R | R | NH2 | | | 47 | 586.3 | 698.2 |
| P11 | 24 | Ac | T G R A | R | NH2 | | | 45 | 600.3 | 712.2 |
| P12 | 25 | Ac | T G K K | K | NH2 | | | 10 | 601.4 | 713.3 |
| P13 | 26 | H | T G R R | R | NH2 | | | 95 | 643.5 | 755.3 |
| P14 | 27 | Ac | T G R R | R | CO2 | | | 56 | 686.4 | 798.2 |
| P15 | 39 | Ac | R R R G | T | NH2 | | | 75 | 685.4 | 797.3 |

[a] The labelling Yield was calculated as (1-f), were f is the fraction of unreacted peptide quantified by HPLC in the $^{99(m+g)}$Tc labelling experiment with protocol 2. SD: Taken into account the uncertainty on the integration of the HPLC peaks, the Inventors assume an uncertainty below 10% on the calculated labelling yields.

Peptides TGRAK (P2) (SEQ ID NO: 15), TGRAKR (P3) (SEQ ID NO: 16) and TGRAKRR (P4) (SEQ ID NO: 17) corresponded respectively to the first 5, 6 and 7 N-terminal residues of the parent sequence UBI 29-41 (SEQ ID: NO 1). The [TcO]$^{3+}$ labelling yields obtained for P2, P3 using protocol 2 were respectively 40, 67%. The above observations clearly showed that the K5-R6 pair played a significant role in the [TcO]$^{3+}$ chelation efficiency as the presence of these two residues led to an important increase in labelling efficiency as compared to the TGRA sequence (SEQ ID NO: 14). In contrast, the comparison of the results obtained for peptide P3 and P4 showed that residue R7 did not significantly improve the [TcO]$^{3+}$ labelling yield. This was further confirmed by the [TcO]$^{3+}$ labelling yield determined for peptide P5, where the residue R7 was replaced by a Norvaline, that was similar to that obtained for peptide P4 and P3. The above results show that the determinants for an efficient [TcO]$^{3+}$ chelation in the peptides UBI 29-41 (SEQ ID NO: 1) are present in the N terminal hexapeptide of the native sequence. In order to further investigate the particular role of each position in this hexapeptide, the Inventors synthesized a second series of shorter peptides and evaluated their [TcO]$^{3+}$ chelation labelling yields.

As demonstrated previously, the pair of basic residues $K_5$-$R_6$ has a role in the [TcO]$^{3+}$ chelation efficiency. Peptide P6 was synthesized to evaluate the impact of the substitution of the Lysine in position 5 by an Arginine residue. As shown in table IV, a significant increase of the [TcO]$^{3+}$ labelling yield by about 20% was observed as compared to P3. This observation showed that, despite their shared basic character, Lysine and Arginine might have a different impact in determining the [TcO]$^{3+}$ chelation efficiency in the conditions of protocol 1 In addition, the dramatic decrease of the [TcO]$^{3+}$ labelling yield observed for peptide P7(TGRAAR) (SEQ ID NO: 20) by about 60% as compared to P6 (TGRARR) (SEQ ID NO: 19) suggests that the number of Arginines and/or the position of these basic residues in the sequence has a strong influence on the labelling yield.

In order to obtain shorter [TcO]$^{3+}$ chelation peptides, the inventors synthesized several peptides incorporating the [TcO]$^{3+}$ chelation determinants identified above. These include the presence of the [TcO]$^{3+}$ chelating function, namely the hydroxyl function of $T_1$, and the 3 NH amide of residues in position 2, 3 and 4 and at least a pair of basic residues. The minimal sequence possessing all these determinants corresponds to peptide P8 (TGRR) (SEQ ID NO: 21). The labelling yield determined for P8 was however only about 40% that was only half the yield observed for P6. This suggested that, despite the presence of the determinants identified previously, other factors play a role in the [TcO]$^{3+}$ chelation efficiency in P6. The Inventors therefore synthesized peptide P9 (TGRRR) (SEQ ID NO: 22) possessing the first 3 N terminal residues of UBI 29-41 (SEQ ID: NO 1) and the Arginine pair in position 4-5. The presence of residue $R_3$ in P9 led to a significant increase about 25% as compared to P8 (TGRR) (SEQ ID NO: 21). This prompted the inventors to synthesized peptide P10 to evaluate if there was a specific contribution of the guanidinium of $R_3$ or if this residue played a role of spacer between the chelating motif and the Arginine pair in P9. The [TcO]$^{3+}$ labelling yield for peptide P10 (TGGRR) (SEQ ID NO: 23) was significantly reduced as compared to peptide P9 by about 20% suggesting a specific role of residue R$_3$ in this sequence. In addition, the similar labelling yields obtained for peptide P10 (TGGRR) (SEQ ID NO: 23), P11 (TGRAR) (SEQ ID NO: 24) and P2 (TGRAK) (SEQ ID NO: 15) about 50% were consistent with the previous conclusion that a pair of basic residue in either vicinal position or separated by one residue led to a significant improvement of the [TcO]$^{3+}$ labelling yield as compared to the tetrapeptide sequence TGRA (SEQ ID NO: 14) (peptide P1).

In order to confirm the specific role of Arginine residues in P9 (TGRRR) (SEQ ID NO: 22), the Inventors synthesized peptide P12 (TGKKK) (SEQ ID NO: 25). The very low [TcO]$^{3+}$ labelling yield determined for P12 clearly demonstrated the specific contribution of the guanidinium groups in P9 as compared to the ammonium groups in the side chains of residue 3 to 5 in P12 in the conditions of protocol 2.

The application of the peptides sequences identified in the present work concerns the labelling of peptides and proteins. Such [TcO]$^{3+}$ chelating peptide sequence could be incorporated to the protein in N or C terminal position. Therefore it was important to evaluate the impact of a free N or C-terminal on the [TcO]$^{3+}$ chelating sequence reported above. To this end, the inventors synthesized peptides P13 and P14 that possessed respectively a free amino and a carboxyl terminal group. The increase of the [TcO]$^{3+}$ labelling yield determined for P13 as compared to P9 by about 25% demonstrated that the free amino terminal in P13 improved significantly the chelation efficiency. This peptide might therefore be used to tag proteins or peptides in N-terminal position and could lead to an almost quantitative incorporation of the [TcO]$^{3+}$ core in the conditions of protocol 2. A similar effect on the [TcO]$^{3+}$ labelling yield of the deletion of N-terminal acetyl group was observed in UBI 29-41 (H-UBI (SEQ ID: NO 13) versus UBI-WT (SEQ ID: NO 1) in Table I. Even less efficient as compared to P13, the significant [TcO]$^{3+}$ labelling of peptide P14 suggest the TGRRR (SEQ ID NO: 26) sequence could be used to tag proteins or peptide in C-terminal position. The Inventors also investigated the retro inverso sequence of P9 (RRRGT, (SEQ ID NO: 39)) peptide P15. The [TcO]$^{3+}$ labelling yield obtained for P15 in the conditions of protocol 2 suggested that this sequence could also be used as a C-terminal tag to incorporate [TcO]$^{3+}$ in proteins or peptides.

The above results allowed defining short efficient [TcO]$^{3+}$ chelating peptide sequences. Among the sequences reported, the TGRRR sequence (peptide P13) (SEQ ID NO: 23) was the most efficient leading to an almost quantitative incorporation of the [TcO]$^{3+}$ core in the conditions of protocol 2. The observation that the presence of a free N-terminal group in the TGRRR sequence (SEQ ID NO: 23) improved significantly the [TcO]$^{3+}$ labelling yield as compared to a N-acetyl group (P13 versus P9) prompted the inventors to identify the [TcO]$^{3+}$ coordinating functions in P13. To this end, the NMR study of the free form of peptide P13 and its complex with the [TcO]$^{3+}$ core was undertaken. A set of $^1$H-$^1$H TOCSY, $^1$H-$^1$H ROESY and $^1$H-$^{13}$C HSQC-TOCSY experiments allowed the assignment of most of the $^1$H and $^{13}$C resonances in the two forms. As observed in the case of UBI 29-41 (SEQ ID NO: 1), several NH resonances were absent in the TcO[TGRRR] complex as compared to the free peptide. These correspond to residue G$_2$, R$_3$ and A$_4$.

The comparison of the $^1$H and $^{13}$C chemical shifts of P13 in the free form and in complex with [TcO]$^{3+}$, reported in Table V and VI, gave some indications on the [TcO]$^{3+}$ chelating functions.

TABLE V $^1$H and $^{13}$C (in parentheses) NMR chemical shift assignments$^a$ of the HTGRRR peptide (P13).

| | HN | αCH | βCH | Others |
|---|---|---|---|---|
| T$_1$ | 7.72 | 4.12(59.44) | 3.67(67.40) | γCH3: 1.29(18.58) |
| G$_2$ | n.d.$^b$ | 3.98(42.45) | | |
| R$_3$ | 8.41 | 4.29(53.46) | 1.73/1.82 (28.25) | γ: 1.62(24.45); δ: 3.38(40.70); ε: 7.17 |
| R$_4$ | 8.43 | 4.30(53.34) | 1.60/1.72(28.20) | γ: 1.60(24.40); δ: 3.16(40.68); ε: 7.15 |
| R$_5$ | 7.60 | 4.26(50.33) | 2.37(30.83) | γ: 1.99(17.12); δ: 3.44(40.70); ε: 7.00; NH2 Cter: 8.79 |

$^a$Chemical shift were reference relative to TSP and were measured at 298K.
$^b$n.d.: not determined.

TABLE VI $^1$H and $^{13}$C (in parentheses) NMR chemical shift assignments$^a$ of the TcO[HTGRRR] complex (P13).

| | HN | αCH | βCH | Others |
|---|---|---|---|---|
| T$_1$ | 8.41 | 4.12(72.14) | 4.26(75.49) | γCH3: 1.28(19.75) |
| G$_2$ | — | 4.47/4.62(56.56) | | |
| R$_3$ | — | 4.41(63.96) | 1.99/2.17 (31.13) | γ: 1.55/1.83(23.61); δ: 3.19(41.68); η: 7.15 |
| R$_4$ | — | 5.12(58.90) | 2.21/2.16(29.11) | γ: 1.57(25.16); δ: 3.24(41.57); η: 7.13 |
| R$_5$ | 7.58 | 4.24(53.23) | 1.58/1.74(29.00) | γ: 1.16(25.02); δ: 2.84/3.11(41.11); η: 6.99; NH2 Cter: 8.79 |

$^a$Chemical shift were reference relative to TSP and were measured at 298K.

Several $^{13}$C resonances displayed important chemical shift changes between the free form of P13 and its [TcO]$^{3+}$ complex. These concern the Cα resonances of residue T$_1$, G$_2$ and R$_3$ that shift respectively by 12.7, 14.1 and 10.50 ppm. In addition, the Cβ resonance of residue T$_1$ shifts by 8.09 ppm and that of residue R$_4$ by 5.56. Such large $^{13}$C chemical shift changes were also observed for 3 carbons in the TcO[UBI 29-41] complex, namely, the Cβ carbon of T$_1$ and the Cα carbon of R$_3$ and A$_4$, and these shifts were assumed to be due to the direct involvement adjacent atoms in the coordination of the [TcO]$^{3+}$ core.

These $^{13}$C shift in conjunction with the absence of the NH resonance of residue G$_2$, R$_3$ and A$_4$ led the inventors to conclude that these three nitrogens and the oxygen of the OH group of T$_1$ were the four chelating atoms of the [TcO]$^{3+}$ core. In peptide P13, the situation appears more complex as 5 carbons display significant chemical shift change between the free form and its [TcO]$^{3+}$ complex. This observation suggests that, in contrast to the situation depicted in UBI 29-41 (SEQ ID NO: 1), five atoms might be involved in the coordination of the [TcO]$^{3+}$ core.

These observations could be compatible with an octahedral coordination of the Tc, the oxygen of the hydroxyl group of T$_1$ being in the square plane or in apical position of the square plane. Alternatively the present data could be compatible with an equilibrium between two structures where 2 sets of four atoms of the peptide might participate in the chelation of the [TcO]$^{3+}$ core. The observation of a single set of $^1$H and $^{13}$C resonances in the NMR spectra, implies that the two structures could be in fast interconversion in the NMR time scale.

The above results allowed the identification of several key elements playing a role in the chelation of the [TcO]$^{3+}$ core in the peptide sequence derived from the UBI 29-41 (SEQ ID: NO 1) N-terminal sequence. In addition to the presence of a residue Threonine that participates in the chelation via its OH group in conjunction with the nitrogen atoms of the amide groups of the adjacent residues, the presence of at least a pair of Arginine residues improves significantly the labelling yield in the pentapeptide sequence.

To be useful for the in vivo application of the TGRRR sequence (SEQ ID NO: 26) to label peptides or proteins, the TcO[TGRRR] (SEQ ID NO: 27) complex must be stable during 1-3 times the period of $^{99m}$Tc. The inventors evaluated the stability of the [TcO]$^{3+}$ complexes in the case of the peptide UBI-WT (SEQ ID: NO 1) and TGRRR, (peptide P13; SEQ ID NO: 26). To this end, the inventors performed a Cysteine challenge. 16 µg of the TcO[UBI-WT] was added to 1, 15, and 100 mM solutions of Cysteine at pH 7.4 corresponding respectively to molar ratio of 3, 53 and 333. These samples were incubated for 20 h at 310 K. The mixtures were analyzed by HPLC and LC-MS.

In the case of UBI-WT, only 10% of the initial [TcO]$^{3+}$ complex were observed in the presence of 100 mM Cysteine after 20 h. However, 69% and more than 95% of the initial complex were observed in the presence of 15 mM and 1 mM Cysteine respectively. In the case of [TGRRR]TcO (SEQ ID NO: 26), 57% of the initial complex was observed in the presence of 15 mM Cysteine after 20 h incubation at 310 K. These observations suggest that these complexes were stable enough to be used for in vivo investigation.

To prove the usefulness, in the field of molecular imaging, of the TGRRR sequence (SEQ ID NO: 26) to label a protein with [TcO]$^{3+}$, the inventors chose aprotinin (BPTI), a natural inhibitor of Serine proteases like trypsin, chymotrypsin, plasmin and kallikrein. It is commercially available under the name of Trasylol (Bayer, Germany). $^{99m}$Tc-aprotinin has been already used to visualize renal morphology (38) and to image amyloid fibrils (20). It has also been recently suggested to be useful for visualizing thrombii via the targeting of the fibrinolytic and/or neutrophile-derived Serine protease activities (39).

Most of the studies using $^{99m}$Tc aprotinin as imaging agents were labelled by the direct approach. It is admitted that this [TcO]$^{3+}$ labelling occur via the reduction of the disulfides. However, examination of the 3D structure of aprotinin in complex with trypsin, demonstrated that one of these disulfide bonds (14-38) is located in a position adjacent to the residue Lysine 15 which plays a key role in the interaction with the Serine proteases targeted (21). In addition this disulfide bond has been recently shown to confer protection against the hydrolysis by one of its targets, trypsin (22). It is therefore highly desirable to label BPTI using a protocol that (1) preserve the disulfides and (2) avoid [TcO]$^{3+}$ chelation at these sites.

The inventors produced, by solid phase chemical synthesis, an analog of BPTI (BPTIv, SEQ ID NO: 32) where the native residue M52 was replaced by a Norleucine to avoid methionine oxydation. The application of protocol 2 used in the present work to label the different peptides was applied to BPTIv (SEQ ID NO: 32). In these conditions, no TcO[BPTIv] complex was formed. The peak observed in HPLC and characterized by ESI-MS corresponded to the uncomplexed BPTIv (Table VII).

TABLE VII

TcO Labelling yield of BPTIv (SEQ ID NO: 32) and TGRRRGG-BPTIv (SEQ ID NO: 33) using protocol 2.

| Protein | TcO Labelling Yield | MW |
|---|---|---|
| BPTIv | 0% | 7232.5 |
| TGRRRGG-BPTIv | >95% | 7344.5 |

As the N-terminal sequence of BPTI is located in a region distant from the target by about 30 Å (Distance R1 Cα-K15 Cα, PDB code 2PTC), the inventors produced, by solid phase chemical synthesis, an analog of BPTIv (SEQ ID: NO 32) where the TcO chelating sequence TGRRR (SEQ ID NO: 26) discovered in the present work was added in N terminal position of BPTIv. In addition, a GG spacer was added between the TGRRR (SEQ ID NO: 26) and the first residue of BPTIv in order to avoid putative conformational constraints that could prevent [TcO]$^{3+}$ chelation. This construct, TGRRRGG-BPTIv (SEQ ID NO: 33) was produced by solid phase chemical synthesis and characterized by ESI-MS. The inventors applied the [TcO]$^{3+}$ labelling protocol 2 to TGRRRGG-BPTIv (SEQ ID NO: 33). The HPLC analysis of this sample displayed only one peak and the ESI-MS analysis showed that the mass of the product corresponds to an adduct of +112 Da to the mass of TGRRRGG-BPTIv (SEQ ID NO: 33) (Table VII). In addition, the electronic absorption spectra of the monoadduct exhibited a large absorption centred at 274 nm neither observed in the absorption spectra of the uncomplexed TGRRRGG-BPTIv (SEQ ID NO: 23) nor in the BPTIv. As suggested above, this absorption might correspond to a ligand to metal charge transfer (LMCT). These results indicate that the [TcO]$^{3+}$ labelling yield of TGRRRGG-BPTI (SEQ ID NO: 23) is greater than 95% in the conditions of protocol 2.

2.4 Application of the TGRRR Peptide (SEQ ID NO: 26) for the $^{99m}$Tc Labelling of the Somatostatin Analog RC-121.

To further demonstrate the potential of the $_H$TGRRR peptide sequence (SEQ ID NO: 26) to label targeting molecules and its use for diagnostic imaging, the inventors began work with RC-121 (42), a highly potent ligand of somatostatin receptors SST-2 and SST-5. SST-2 is important as it is expressed in a large number of human tumours (43). During the last decades, considerable work has been put into obtaining artificial high affinity ligands of these receptors for use in radiotherapy and nuclear imaging. RC-121 is a cyclic octapeptide analog of the prototypic somatostatin analog in oncology, octreotide (42). RC-121 corresponds to the sequence $_D$FCY$_D$WKVCT$_{NH2}$ (SEQ ID NO: 40) cyclized via a disulfide between residues $C_2$ and $C_7$ (FIG. 3a).

The inventors modified RC-121 by adding the $_H$TGRRRGG sequence (SEQ ID NO: 34) in its N-terminal position, the GG dipeptide being introduced as a spacer (FIG. 3b). Using the same TcO labelling conditions described above to study the short peptides derived from UBI 29-41, the inventors obtained a quantitative incorporation of the TcO core in $_H$TGRRRGG-RC-121 (SEQ ID NO: 41) with the preservation of the disulfide bridge as evaluated by LC-MS (Table VIII).

TABLE VIII

Binding of RC-121, $_H$TGRRRGG-RC-121 and its TcO complex to the AR2-2J cells and the somatostatin receptors.

| Compound | Ki (pM) | Receptor/Cells |
|---|---|---|
| RC-121 | 100 | CHO-SST-2 (mb) |
|  | 300 | AR4-2J (cells) |
| $_H$TGRRRGG-RC-121 | 20 | CHO-SST-2 (mb) |
|  | 35 | AR4-2J (cells) |
| TcO[$_H$TGRRRGG-RC-121] | 20 | CHO-SST-2 (mb) |
| (SEQ IN NO: 41) | 66 | AR4-2J (cells) |
|  | 58000 | CHO-SST-1 (mb) |
|  | 10000 | CHO-SST-3 (mb) |
|  | 110000 | CHO-SST-4 (mb) |
|  | 30000 | CHO-SST-5 (mb) |

A control experiment also showed that the untagged RC-121 was unable to form a TcO complex in these labelling conditions. The stability of this complex determined in the presence of 15 mM cysteine was similar to that observed for the TcO[$_H$TGRRR] (SEQ ID NO: 27) complex. About 70% and 60% of the complex was still present after 4 hours and 24 hours incubation at 310 K.

The binding of the TcO[$_H$TGRRRGG-RC-121] (SEQ ID NO: 41) complex with the somatostatin receptors was then characterized. These experiments showed that the insertion of the $_H$TGRRRGG (SEQ ID NO: 34) sequence in RC-121 did not reduce its binding capacity for the SST-2 receptor (Table IX).

TABLE IX

LC-MS analysis of $_H$TGRRRGG-RC-121 and its complex with TcO.

|  | MW Calc (D) | MW Exp (D) |
|---|---|---|
| $_H$TGRRRGG-RC-121 | 1785.8 | 1786.6 |
| TcO[$_H$TGRRRGG-RC-121] | 1897.8 | 1898.4 |

The $K_d$ of TcO[$_H$TGRRRGG-RC-121] (SEQ ID NO: 41) for SST-2 ($K_d$/SST-2: 20 pM) was about 5 times lower than that determined for RC-121. In addition, the inventors showed that TcO[$_H$TGRRRGG-RC-121] (SEQ ID NO: 41) is a selective ligand of SST-2 receptors by a factor ranging from about 100 for SST-5 to about 5000 for SST-4 (Table IX).

The TcO[$_H$TGRRRGG-RC-121] (SEQ ID NO: 41) complex was evaluated as an imaging agent in a mouse xenografted tumour model. For this model, the inventors selected the AR4-2J tumour cell line that is known to express the SST-2 somatostatin receptor. The $K_d$ of TcO[$_H$TGRRGG-RC-121] (SEQ ID NO: 41) for the AR4-2J cells was 60 pM (Table X).

A First group of AR4-2J xenografted mice were injected with the $^{99(m+g)}$TcO[$_H$TGRRRGG-RC-121](SEQ ID NO: 41). Two control experiments were also conducted. AR4-2J-bearing nude-mice (group 2) were injected with the $^{99(m+g)}$TcO[$_H$TGRRRGG-RC-121] (SEQ ID NO: 41) and a 125 fold excess of the unlabelled RC-121 compound. A third group of AR4-2J-bearing nude-mice were injected with the $^{99(m+g)}$TcO[$_H$TGRRR] (SEQ ID NO: 27) complex as a control experiment (group 3). The biodistribution of $^{99(m+g)}$TcO[$_H$TGRRR] (SEQ ID NO: 27) in the 3 groups was determined 4 hours after injection are shown in Table X.

TABLE X

Biodistribution of the $^{99m}$TcO labelled compound in the AR4-2J xenografted nude-mice 4 h after injection. The radioactivity measured is expressed in % ID/g (percent of the injected dose by gram of tissue). Each group corresponded to 6 mice.

| Organ | TcO[$_H$TGRRRGG-RC-121] (SEQ ID NO: 41) Unblocked | TcO[$_H$TGRRRGG-RC-121] (SEQ ID NO: 41) Blocked | TcO[$_H$TGRRR] (SEQ ID NO: 27) |
|---|---|---|---|
| Urine | 24.4 ± 9.2 | 38.7 ± 62.8 | 8.6 ± 5.5 |
| Blood | 0.1 ± 0.1 | 0.1 ± 0.1 | 0.3 ± 0.3 |
| Pancreas | 1.1 ± 0.4 | 0.3 ± 0.3 | 0.3 ± 0.6 |
| Spleen | 1.2 ± 0.2 | 1.0 ± 0.7 | 0.7 ± 0.6 |
| Adrenals | 1.7 ± 2.8 | 9.4 ± 8.2 | 2.2 ± 4.7 |
| Kidneys | 188.9 ± 17.3 | 87.0 ± 7.3 | 21.9 ± 9.5 |
| Bile | 2.2 ± 5.9 | 4.8 ± 6.9 | 6.6 ± 2.4 |
| Heart | 0.1 ± 0.3 | 0.8 ± 0.8 | 0.7 ± 0.6 |
| Lungs | 1.1 ± 0.5 | 0.7 ± 0.2 | 0.6 ± 0.8 |
| Liver | 15.5 ± 1.3 | 7.8 ± 0.9 | 2.1 ± 0.5 |
| Tumor | 5.3 ± 1.3 | 0.7 ± 0.2 | 0.3 ± 0.1 |
| Brain | 0.0 ± 0.0 | 0.1 ± 0.0 | 0.1 ± 0.2 |
| Intestines | 1.2 ± 0.8 | 1.2 ± 1.0 | 1.3 ± 0.8 |
| Stomach | 1.2 ± 0.5 | 0.3 ± 0.1 | 2.6 ± 2.2 |
| Muscle | 0.2 ± 0.4 | 0.1 ± 0.6 | 0.8 ± 1.23 |
| Tail | 1.0 ± 0.6 | 2.1 ± 0.8 | 5.3 ± 4.5 |
| Carcass | 0.3 ± 0.0 | 0.3 ± 0.0 | 0.2 ± 0.1 |
| Tumor/Muscle Ratio | 26.5 | 7 | 2.6 |
| Tumor/Blood Ratio | 53.0 | 7 | 1 |

In the case of group 1, the % ID/g determined for most organs were about 1% ID/g or below. As expected, urine, kidney and liver corresponded to the most important radioactivity uptake. However, apart from these compartments, the most important uptake of TcO[$_H$TGRRRGG-RC-121] (SEQ ID NO: 41) is observed in the tumour (% ID/g=5.3±1.3). In the presence of a 125-fold excess of RC-121, the most important radioactivity uptakes are also observed in the urine and kidney and to a lesser extent in adrenals and liver. However, in the mice of group 2, the % ID/g determined for the tumour is significantly lower than that determined in group 1 (% ID/g=0.7±0.2).

These observations show that the presence of a 125-fold excess of RC-121, a nanomolar SST-2 ligand reduced significantly TcO[$_H$TGRRRGG-RC-121] (SEQ ID NO: 41) tumour uptake. The control experiment (group 3) corresponding to the biodistribution of the TcO[$_H$TGRRR] (SEQ ID NO: 27) peptide complex in AR4-2J bearing mice demonstrated no significant radioactivity uptake in the tumour. The capacity of the TcO[$_H$TGRRRGG-RC-121] (SEQ ID NO: 41) complex to image the AR4-2J xenografted tumour can be characterized by the tumour/muscle ratio and the tumour/blood ratio that are respectively 26.5 and 53. Significantly lower tumour/muscle and tumour/blood ratios are observed in groups 2 (7 and 7 respectively) and 3 (2.6 and 1 respectively) as compared to group 1. Overall, these results demonstrated specific and high tumour uptake of the TcO[$_H$TGRRRGG-RC-121] (SEQ ID NO: 41) compound in the AR4-2j tumour.

To demonstrate the potential of the $^{99(m+g)}$TcO[$_H$TGRRRGG-RC-121] (SEQ ID NO: 21) for diagnostic imaging, the inventors analyzed a whole body section of a mice of group 1 (FIG. 4A, B). FIG. 4A, B shows that, according to the results obtained from the biodistribution of $^{99(m+g)}$TcO[$_H$TGRRRGG-RC-121](SEQ ID NO: 21), the most important radioactivity uptakes are located at the level of the kidney and the liver. The picture of the section analyzed allows unambiguous location of the tumour and the β-imaging of this section demonstrated the important uptake of the labelled compound in this region. Comparison of this section with that obtained with section of a mice belonging to group 2 (FIG. 4 C, D) confirmed the absence of radioactivity uptake in the presence of 125-fold excess of RC-121. These results demonstrate the capacity of the $^{99(m+g)}$TcO[HTGRRRGG-RC-121] (SEQ ID NO: 21) compound for imaging of SST-2 expressing tumours and suggest that the $_H$TGRRR (SEQ ID NO: 22) peptide offers an attractive way of labelling virtually any targeting peptides and proteins with technetium for in vivo diagnostic applications.

3. Conclusions

The first part of the inventors work concerned the analysis of the [TcO]$^{3+}$ chelation site of a tri-decamer fragment of the protein ubiquicidin, named UBI 29-41.

In the present work, to determine the fraction of [TcO]$^{3+}$ labelled peptide, as well as to identify the residues and the chemical functions involved in the chelation of the [TcO]$^{3+}$ core, the inventors designed a [TcO]$^{3+}$ labelling protocol using 5.5 mM aqueous solution of NH$_4$TcO$_4$ as source of $^{99}$Tc. This allowed working with slight excess of TcO$_4^-$ (1.5 equivalent) as compared to the peptide concentration in the 100 μM range. The resulting labelling yields for UBI 29-41 and its analogs range from about 30% to 95% of the peptides and they were thus quantified with a reasonable precision estimated below 10%. In addition, this labelling protocol allowed the production of sufficient amounts of labelled peptides to undertake the NMR analysis of some of the [TcO]$^{3+}$ peptide complexes.

Regarding the labelling efficiency, the results for the different analogs of UBI 29-41 that the inventors have developed showed that the replacement of residue T$_1$ by an aminobutyric acid and the significant decrease in the [TcO]$^{3+}$ labelling yield strongly suggested the direct implication of the hydroxyl group of T$_1$ in the coordination of the [TcO]$^{3+}$ core. None of the other analogs displayed such a dramatic decrease and their labelling yields ranged between 78 and 93%. This strongly suggested that none of the chemical functions of residue R$_3$ to R$_{13}$ in UBI 29-41 appear to directly participate in the coordination of the [TcO]$^{3+}$ core. This interpretation was confirmed by the results of the NMR analysis of the TcO[UBI 29-41].

In this study, the observation that the amide proton resonances of residue G$_2$, R$_3$ and A$_4$, observed at the free state were absent in the complex, suggested that these amide groups were involved in the coordination of the [TcO]$^{3+}$ core. In addition, the large $^{13}$C downfield chemical shifts changes as compared to the free peptide (in the 10 ppm range) of the Cα of residues G$_2$, R$_3$ and A$_4$ and of the Cβ of residue T$_1$ allowed the inventors to propose that the [TcO]$^{3+}$ core was coordinated by the amide nitrogen of residue G$_2$, R$_3$ and A$_4$ and the oxygen of the hydroxyl group of T$_1$ in the TcO[UBI 29-41] complex. Other NMR evidences like the non-equivalence of the resonances of the Hα1/Hα2 of G$_2$ in the TcO[UBI 29-41] sustained this interpretation. Downfield $^1$H chemical shift changes of the Hα resonances of residue T$_1$ and R$_3$ upon complex formation were also observed in UBI 29-41.

It must be noted that the peptide UBI 29-41 in the complex studied by NMR was N-acetylated (UBI-WT, Table I). The non-acetylated version of UBI 29-41 (H-UBI) displayed an unexpected significantly increased [TcO$^{3+}$] labelling yield as compared to the N-acetytated one. This suggests that the N-terminal group might play a direct role in the chelation of the TcO core in H-UBI.

The present work allowed the Inventors to identify the [TcO$^{3+}$] coordination site in UBI 29-14 to the N terminal part of the peptide (Residue 1-4) and that the coordination atoms are oxygen of the hydroxyl group of T1 and the nitrogen of the amide function of residue G2, R3 and A4.

The discovery that the [TcO]$^{3+}$ chelation site was located in the N terminal segment corresponding to residues 1-4 of the UBI 29-41 (SEQ ID NO: 1) prompted the inventors to search for a minimal [TcO]$^{3+}$ chelating sequence derived from UBI 29-41. The aim of this part of the work was two fold (1): analyzing in detail the determinants of the [TcO]$^{3+}$ chelating in UBI 29-41 and (2) defining a shorter efficient [TcO]$^{3+}$ chelating peptide sequences that could be incorporated at the N-terminal or C-terminal side of a bioactive peptide or protein to design imaging agents.

The results obtained regarding the chelation of [TcO]$^{3+}$ by the N-terminal tetrapeptide sequence of UBI 29-41 clearly indicated that other factors than the coordinating functions play a role in determining the [TcO]$^{3+}$ labelling yield. This prompted the inventors to synthesize a series of tetra, penta and hexapeptides possessing a Threonine in N-terminal position. The NMR study of pentapeptide P13 demonstrated that the N-terminal Threonine was directly involved in the coordination of the [TcO]$^{3+}$ core. The inventors therefore assume that all the peptides synthesized in the present study chelate the [TcO]$^{3+}$ core via their N-terminal sequence, where the oxygen of the hydroxyl group of T$_1$ is always present. This oxygen may constitute one of the driving forces that determine the location of the [TcO]$^{3+}$ chelation site in these peptides. It must be noted that the NMR data recorded on the [TcO]$^{3+}$ complex of peptide P13 strongly suggest that, in addition to the coordinating functions identified in peptide P9, the N-terminal group might participate in the coordination of the [TcO]$^{3+}$ core. This may explain the almost quantitative incorporation of the [TcO]$^{3+}$ core observed for peptide P13 that is significantly increased as compared to the N-acetyl version P9 of this sequence.

The inventors pointed out that the presence of residues adjacent to the N3O chelating sequence have a strong impact of the [TcO]$^{3+}$ labelling yield of the peptides in protocol 2. In particular they identified the role of Arginine residues adjacent to the [TcO]$^{3+}$ chelating site. It has been demonstrated that a pair of Arginines located in the vicinity of the chelating site significantly improved the [TcO]$^{3+}$ labelling yield in the conditions of protocol 2. One may suggest that the Arginine residues play a role in the [TcO]$^{3+}$ chelation efficiency via their guanidinium groups. In the present context, the TcO$_4^-$ anions may interact with the guanidinium groups of the Arginines located in the vicinity of the chelating site prior to reduction. Consistent with this interpretation is the comparison of the [TcO]$^{3+}$ labelling yield of peptide P9 that is dramatically increased (by about 60%) as compared to P12 (Table IV) suggesting that Arginine residues may have a specific contribution beyond their cationic character. The present data does not allow a definitive description of the precise mechanism by which the segment R3 to R5 of the TGRRR SEQ ID NO: 26) peptide improves the [TcO]$^{3+}$ labelling yield dramatically. However the inventors might propose that the Arginines could stabilise the TcO$_4^-$ in a manner similar to the co-ligand used in the ligand exchange approach. Consistent with this proposal is the fact that the [TcO]$^{3+}$ labelling protocol 2, implies the simultaneous reduction of the pertechnetate oxyanion and the coordination of the resulting [TcO]$^{3+}$ core.

The most efficient pentapeptide discovered in the present work is pentapeptide peptide P13 (TGRRR; SEQ ID NO: 26). As a proof of concept of the [TcO]$^{3+}$ labelling of a protein with the TGRRR sequence (SEQ ID NO: 26), the inventors considered aprotinin, a natural inhibitor of Serine proteases like trypsin, chymotrypsin, plasmin and kallikrein. The application of the [TcO]$^{3+}$ labelling protocol 2 used in the present work to TGRRRGG-BPTIv (SEQ ID NO: 33) showed a quantitative incorporation of the [TcO]$^{3+}$ core while no [TcO]$^{3+}$ labelling was observed in the same conditions with BPTIv. In addition, these experiments demonstrated that the [TcO]$^{3+}$ labelling protocol used in the present study did not affect the disulfide bridges that are essential for the preservation of the 3D structure and consequently for the binding capacity of proteins. This application demonstrates the value of the TGRRR (SEQ ID NO: 26) tag in conjunction with protocol 2 to label proteins of interest in the field of molecular imaging.

A very attractive point regarding the sequences described in the present report is that they are composed of natural amino acids. Therefore, their use is not limited to proteins produced by solid-phase peptide synthesis but can be easily incorporated to large size protein via recombinant technologies. Such peptide sequences can be added to the N-terminal or the C-terminal sequence of the targeting molecule, if this region is not involved in the interaction with its receptor.

To the inventors knowledge, this is the first efficient N3O [TcO]$^{3+}$ chelating peptide sequence described. In addition, the labelling yield obtained in the conditions of the inventors protocol 2 with the N-acetylated version as well as the N-terminal free sequence shows that both versions of the TGRRR (SEQ ID NO: 26 and SEQ ID NO: 22) tag could be used to label efficiently peptides and proteins. Furthermore, the reverse sequence AcRRRGT (P15) (SEQ ID NO: 39) that display similar [TcO]$^{3+}$ labelling yield as the TGRRR sequence (P9) (SEQ ID: NO 22) could be used to label peptides and proteins at their C-terminal sides. Applications of this approach to the Serine proteases inhibitor BPTI demonstrated that the TGRRR tag added in N-terminal position of the protein lead to a quantitative incorporation of the [TcO]$^{3+}$ core. These results open considerable perspectives regarding the use of protein produced by solid phase chemical synthesis as well as recombinant technologies as $^{99m}$Tc imaging agents.

REFERENCES (1) Rhodes, B. A. *Int J Rad Appl Instrum B* 1991, 18, 667-76.
(2) Hnatowich, D. J.; Mardirossian, G.; Rusckowski, M.; Fogarasi, M.; Virzi, F.; Winnard, P., Jr. *J Nucl Med* 1993, 34, 109-19.
(3) Larsen, S. K.; Solomon, H. F.; Caldwell, G.; Abrams, M. J. *Bioconjug Chem* 1995, 6, 635-8.
(4) Liu, S.; Edwards, D. S.; Looby, R. J.; Harris, A. R.; Poirier, M. J.; Barrett, J. A.; Heminway, S. J.; Carroll, T. R. *Bioconjug Chem* 1996, 7, 63-71.
(5) Kasina, S.; Rao, T. N.; Srinivasan, A.; Sanderson, J. A.; Fitzner, J. N.; Reno, J. M.; Beaumier, P. L.; Fritzberg, A. R. *J Nucl Med* 1991, 32, 1445-51.
(6) Kasina, S.; Sanderson, J. A.; Fitzner, J. N.; Srinivasan, A.; Rao, T. N.; Hobson, L. J.; Reno, J. M.; Axworthy, D. B.; Beaumier, P. L.; Fritzberg, A. R. *Bioconjug Chem* 1998, 9, 108-17.
(7) Liu, S.; Edwards, D. S. *Chem Rev* 1999, 99, 2235-68.
(8) Lister-James, J.; Moyer, B. R.; Dean, T. *Q J Nucl Med* 1996, 40, 221-33.
(9) Lister-James, J.; Knight, L. C.; Maurer, A. H.; Bush, L. R.; Moyer, B. R.; Dean, R. T. *J Nucl Med* 1996, 37, 775-81.
(10) Vanbilloen, H. P.; Bormans, G. M.; De Roo, M. J.; Verbruggen, A. M. *Nucl Med Biol* 1995, 22, 325-38.
(11) Vanbilloen, H. P.; De Roo, M. J.; Verbruggen, A. M. *Eur J Nucl Med* 1996, 23, 40-8.
(12) Perera Pintado, A.; Mather, S. J.; Stalteri, M. A.; Allison, D.; Prats Capote, A.; Hernandez Cairo, A.; Reyes Acosta, O.; Bequet Romero, M. *Journal of Radioanalytical and Nuclear Chemistry* 2008, 275, 619-626.
(13) Tessier, C.; Rochon, F. D.; Beauchamp, A. L. *Inorg Chem* 2004, 43, 7463-73.
(14) Hiemstra, P. S.; van den Barselaar, M. T.; Roest, M.; Nibbering, P. H.; van Furth, R. *J Leukoc Biol* 1999, 66, 423-8.
(15) Welling, M. M.; Paulusma-Annema, A.; Baiter, H. S.; Pauwels, E. K.; Nibbering, P. H. *Eur J Nucl Med* 2000, 27, 292-301.
(16) Welling, M. M.; Lupetti, A.; Batter, H. S.; Lanzzeri, S.; Souto, B.; Rey, A. M.; Savio, E. O.; Paulusma-Annema, A.; Pauwels, E. K.; Nibbering, P. H. *J Nucl Med* 2001, 42, 788-94.
(17) Welling, M. M.; Mongera, S.; Lupetti, A.; Baiter, H. S.; Bonetto, V.; Mazzi, U.; Pauwels, E. K.; Nibbering, P. H. *Nucl Med Biol* 2002, 29, 413-22.
(18) Ferro-Flores, G.; de Maria Ramirez, F.; Melendez-Alafort, L.; de Murphy, C. A.; Pedraza-Lopez, M. *Appl Radial Isot* 2004, 61, 1261-8.
(19) Melendez-Alafort, L.; Ramirez Fde, M.; Ferro-Flores, G.; Arteaga de Murphy, C.; Pedraza-Lopez, M.; Hnatowich, D. J. *Nucl Med Biol* 2003, 30, 605-15.
(20) Cardoso, I.; Pereira, P. J.; Damas, A. M.; Saraiva, M. J. *Eur J Biochem* 2000, 267, 2307-11.
(21) Marquart, M.; Walter, J.; Deisenhofer, J.; Bode, W.; Huber, R. *Acta Crystallogr., Sect B* 1983, 39, 480-490.
(22) Zakharova, E.; Horvath, M. P.; Goldenberg, D. P. *J Mol Biol* 2008.
(23) Wong, E.; Fauconnier, T.; Bennett, S.; Valliant, J.; Nguyen, T.; Lau, F.; Lu, L. F.; Pollak, A.; Bell, R. A.; Thornback, J. R. *Inorg Chem* 1997, 36, 5799-5808.
(24) Wong, E.; Bennett, S.; Lawrence, B.; Fauconnier, T.; Lu, L. F.; Bell, R. A.; Thornback, J. R.; Eshima, D. *Inorg Chem* 2001, 40, 5695-700.
(25) Francesconi, L. C.; Zheng, Y.; Bartis, J.; Blumenstein, M.; Costello, C.; De Rosch, M. A. *Inorg Chem* 2004, 43, 2867-75.
(26) Bigott-Hennkens, H. M.; Junnotula, S.; Ma, L.; Gallazzi, F.; Lewis, M. R.; Jurisson, S. S. *J Med Chem* 2008, 51, 1223-30.
(27) Lipowska, M.; Hansen, L.; Xu, X.; Marzilli, P. A.; Taylor, A., Jr.; Marzilli, L. G. *Inorg Chem* 2002, 41, 3032-41.
(28) Cantorias, M. V.; Howell, R. C.; Todaro, L.; Cyr, J. E.; Berndorff, D.; Rogers, R. D.; Francesconi, L. C. *Inorg Chem* 2007, 46, 7326-40.
(29) katayev, E., A.; Ustynyuk, Y., A.; Sessler, J., L. *Coordination Chemistry Reviews* 2006, 250, 3004-37.
(30) George, A. J.; Jamar, F.; Tai, M. S.; Heelan, B. T.; Adams, G. P.; McCartney, J. E.; Houston, L. L.; Weiner, L. M.; Oppermann, H.; Peters, A. M. *Proc Natl Acad Sci USA* 1995, 92, 8358-62.
(31) Bogdanov, A., Jr.; Simonova, M.; Weissleder, R. *Biochim Biophys Acta* 1998, 1397, 56-64.
(32) Tait, J. F.; Brown, D. S.; Gibson, D. F.; Blankenberg, F. G.; Strauss, H. W. *Bioconjug Chem* 2000, 11, 918-25.
(33) Levashova, Z.; Backer, M.; Backer, J. M.; Blankenberg, F. G. *Bioconjug Chem* 2008, 19, 1049-54.
(34) Waibel, R.; Alberto, R.; Willuda, J.; Finnern, R.; Schibli, R.; Stichelberger, A.; Egli, A.; Abram, U.; Mach, J. P.; Pluckthun, A.; Schubiger, P. A. *Nat Biotechnol* 1999, 17, 897-901.
(35) Nilges, M.; Clore, G. M.; Gronenborn, A. M. *FEBS Lett* 1988, 239, 129-36.

(36) Schwieters, C. D.; Kuszewski, J. J.; Tjandra, N.; Clore, G. M. *J Magn Reson* 2003, 160, 65-73.
(37) Boyd, G. E., J. Chem. Ed. 1959, Vol 36, pp 3-12.
(38) Rustom, R.; Grime, S.; Maltby, P.; Stockdale, H. R.; Critchley, M.; Bone, J. M. Clin. Sci (Lond) 1992, 83(3), 289-294.
(39) Rustom, R.; Grime, S.; Maltby, P.; Stockdale, H. R.; Critchley, M.; Bone, J. M. Clin. Sci (Lond) 1992, 83(3), 289-294.
(40) R. B. Merrifield (1963). "Solid Phase Peptide Synthesis. I. The Synthesis of a Tetrapeptide". *J. Am. Chem. Soc.* 85 (14): 2149-2154.
(41) Bodansky, M; Bondansky, A. "The Practice of Peptide Synthesis", 1984, Springer-Verlag.
(42) Liebow, C., Reilly, C., Serrano, M. & Schally, A. V. (1989). Somatostatin analogues inhibit growth of pancreatic cancer by stimulating tyrosine phosphatase. *Proc Natl Acad Sci USA* 86, 2003-7.
(43) Reubi, J. C., Waser, B., Schaer, J. C. & Laissue, J. A. (2001). Somatostatin receptor sst1-sst5 expression in normal and neoplastic human tissues using receptor autoradiography with subtype-selective ligands. *Eur J Nucl Med* 28, 836-46.

The invention claimed is:

1. A method of radiolabeling a protein with a peptide tag selected from the group consisting of: SEQ ID NO: 22, SEQ ID NO: 26, SEQ ID NO: 27 and the retro-inverso version thereof,
comprising the steps:
a) the successive adding to an aqueous solution containing said protein and said peptide tag of:
(i) an aqueous solution of a reducing agent under basic pH conditions;
(ii) an aqueous solution of a salt of Tc or Re radionuclide; and
b) incubating the solution obtained in step a) for 1 to 10 minutes at room temperature.

2. The method according to claim 1, wherein said Tc radionuclide is $^{99m}$Tc.

3. The method according to claim 1, wherein said Re radionuclide is $^{186}$Re or $^{188}$Re.

* * * * *

```
                              SEQUENCE LISTING

<160> NUMBER OF SEQ ID NOS: 43

<210> SEQ ID NO 1
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: UBI 29-41

<400> SEQUENCE: 1

Thr Gly Arg Ala Lys Arg Arg Met Gln Tyr Asn Arg Arg
1               5                   10

<210> SEQ ID NO 2
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (1)..(1)
<223> OTHER INFORMATION: X is Amino Butyric Acid

<400> SEQUENCE: 2

Xaa Gly Arg Ala Lys Arg Arg Met Gln Tyr Asn Arg Arg
1               5                   10

<210> SEQ ID NO 3
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (3)..(3)
<223> OTHER INFORMATION: X is Norvaline

<400> SEQUENCE: 3

Thr Gly Xaa Ala Lys Arg Arg Met Gln Tyr Asn Arg Arg
1               5                   10

<210> SEQ ID NO 4
<211> LENGTH: 13
<212> TYPE: PRT
<213> ORGANISM: Artificial
<220> FEATURE:
<223> OTHER INFORMATION: Synthesized
```

```
<220> FEATURE:
<223> OTHER INFORMATION: Peptide Fragment
<220> FEATURE:
<221> NAME/KEY: MISC_FEATURE
<222> LOCATION: (5)..(5)
<223> OTHER INFORMATION: X is Norleucine

<400> SEQUENCE: 4

Thr Gly Arg Ala Xaa Arg Arg Met Gln Tyr Asn Arg Arg
1               5                   10

<210> SEQ ID NO 5
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (6)..(6)
<223> OTHER INFORMATION: X is Norvaline

<400> SEQUENCE: 5

Thr Gly Arg Ala Lys Xaa Arg Met Gln Tyr Asn Arg Arg
1               5                   10

<210> SEQ ID NO 6
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (7)..(7)
<223> OTHER INFORMATION: X is Norvaline

<400> SEQUENCE: 6

Thr Gly Arg Ala Lys Arg Xaa Met Gln Tyr Asn Arg Arg
1               5                   10

<210> SEQ ID NO 7
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (8)..(8)
<223> OTHER INFORMATION: X is Norleucine

<400> SEQUENCE: 7

Thr Gly Arg Ala Lys Arg Arg Xaa Gln Tyr Asn Arg Arg
1               5                   10

<210> SEQ ID NO 8
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
```

```
<220> FEATURE:
<221> NAME/KEY: MISC_FEATURE
<222> LOCATION: (9)..(9)
<223> OTHER INFORMATION: X is Amino Butyric Acid

<400> SEQUENCE: 8

Thr Gly Arg Ala Lys Arg Arg Met Xaa Tyr Asn Arg Arg
1               5                   10

<210> SEQ ID NO 9
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 9

Thr Gly Arg Ala Lys Arg Arg Met Gln Phe Asn Arg Arg
1               5                   10

<210> SEQ ID NO 10
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (11)..(11)
<223> OTHER INFORMATION: X is Amino Butyric Acid

<400> SEQUENCE: 10

Thr Gly Arg Ala Lys Arg Arg Met Gln Tyr Xaa Arg Arg
1               5                   10

<210> SEQ ID NO 11
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (12)..(12)
<223> OTHER INFORMATION: X is Norvaline

<400> SEQUENCE: 11

Thr Gly Arg Ala Lys Arg Arg Met Gln Tyr Asn Xaa Arg
1               5                   10

<210> SEQ ID NO 12
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (13)..(13)
<223> OTHER INFORMATION: X is Norvaline
```

<400> SEQUENCE: 12

Thr Gly Arg Ala Lys Arg Arg Met Gln Tyr Asn Arg Xaa
1               5                   10

<210> SEQ ID NO 13
<211> LENGTH: 13
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (1)..(1)
<223> OTHER INFORMATION: Free N-terminus
<220> FEATURE:
<221> NAME/KEY: MISC_FEATURE
<222> LOCATION: (13)..(13)
<223> OTHER INFORMATION: Free C-terminus

<400> SEQUENCE: 13

Thr Gly Arg Ala Lys Arg Arg Met Gln Tyr Asn Arg Arg
1               5                   10

<210> SEQ ID NO 14
<211> LENGTH: 4
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 14

Thr Gly Arg Ala
1

<210> SEQ ID NO 15
<211> LENGTH: 5
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 15

Thr Gly Arg Ala Lys
1               5

<210> SEQ ID NO 16
<211> LENGTH: 6
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 16

Thr Gly Arg Ala Lys Arg
1               5

<210> SEQ ID NO 17
<211> LENGTH: 7
<212> TYPE: PRT
<213> ORGANISM: Artificial

```
<220> FEATURE:
<223> OTHER INFORMATION: Synthesized
<220> FEATURE:
<223> OTHER INFORMATION: Peptide Fragment

<400> SEQUENCE: 17

Thr Gly Arg Ala Lys Arg Arg
1               5

<210> SEQ ID NO 18
<211> LENGTH: 7
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (7)..(7)
<223> OTHER INFORMATION: X is Norvaline

<400> SEQUENCE: 18

Thr Gly Arg Ala Lys Arg Xaa
1               5

<210> SEQ ID NO 19
<211> LENGTH: 6
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 19

Thr Gly Arg Ala Arg Arg
1               5

<210> SEQ ID NO 20
<211> LENGTH: 6
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 20

Thr Gly Arg Ala Ala Arg
1               5

<210> SEQ ID NO 21
<211> LENGTH: 4
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 21

Thr Gly Arg Arg
1

<210> SEQ ID NO 22
<211> LENGTH: 5
<212> TYPE: PRT
<213> ORGANISM: Artificial
```

```
<220> FEATURE:
<223> OTHER INFORMATION: Synthesized
<220> FEATURE:
<223> OTHER INFORMATION: Peptide Fragment

<400> SEQUENCE: 22

Thr Gly Arg Arg Arg
1               5

<210> SEQ ID NO 23
<211> LENGTH: 5
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 23

Thr Gly Gly Arg Arg
1               5

<210> SEQ ID NO 24
<211> LENGTH: 5
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 24

Thr Gly Arg Ala Arg
1               5

<210> SEQ ID NO 25
<211> LENGTH: 5
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 25

Thr Gly Lys Lys Lys
1               5

<210> SEQ ID NO 26
<211> LENGTH: 5
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (1)..(1)
<223> OTHER INFORMATION: Free N-Terminus

<400> SEQUENCE: 26

Thr Gly Arg Arg Arg
1               5

<210> SEQ ID NO 27
<211> LENGTH: 5
<212> TYPE: PRT
<213> ORGANISM: Artificial
```

```
<220> FEATURE:
<223> OTHER INFORMATION: Synthesized
<220> FEATURE:
<223> OTHER INFORMATION: Peptide Fragment
<220> FEATURE:
<221> NAME/KEY: MISC_FEATURE
<222> LOCATION: (5)..(5)
<223> OTHER INFORMATION: Free C-terminus

<400> SEQUENCE: 27

Thr Gly Arg Arg Arg
1               5

<210> SEQ ID NO 28
<211> LENGTH: 3
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 28

Gly Gly Cys
1

<210> SEQ ID NO 29
<211> LENGTH: 3
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 29

Lys Gly Cys
1

<210> SEQ ID NO 30
<211> LENGTH: 3
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 30

Cys Gly Cys
1

<210> SEQ ID NO 31
<211> LENGTH: 4
<212> TYPE: PRT
<213> ORGANISM: Artificial
<220> FEATURE:
<223> OTHER INFORMATION: Synthesized
<220> FEATURE:
<223> OTHER INFORMATION: Peptide Fragment

<400> SEQUENCE: 31

Ala Gly Gly Gly
1

<210> SEQ ID NO 32
<211> LENGTH: 58
<212> TYPE: PRT
<213> ORGANISM: Artificial
```

```
<220> FEATURE:
<223> OTHER INFORMATION: Synthesized
<220> FEATURE:
<223> OTHER INFORMATION: BPTI
<220> FEATURE:
<221> NAME/KEY: MISC_FEATURE
<222> LOCATION: (1)..(1)
<223> OTHER INFORMATION: Free N-terminus
<220> FEATURE:
<221> NAME/KEY: MISC_FEATURE
<222> LOCATION: (52)..(52)
<223> OTHER INFORMATION: X is Norleucine

<400> SEQUENCE: 32

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Xaa Arg Thr Cys Gly Gly Ala
    50                  55

<210> SEQ ID NO 33
<211> LENGTH: 65
<212> TYPE: PRT
<213> ORGANISM: Artificial
<220> FEATURE:
<223> OTHER INFORMATION: Synthesized
<220> FEATURE:
<223> OTHER INFORMATION: TGRRRGG-BPTI
<220> FEATURE:
<221> NAME/KEY: MISC_FEATURE
<222> LOCATION: (1)..(1)
<223> OTHER INFORMATION: Free N-terminus
<220> FEATURE:
<221> NAME/KEY: MISC_FEATURE
<222> LOCATION: (59)..(59)
<223> OTHER INFORMATION: X is Norleucine

<400> SEQUENCE: 33

Thr Gly Arg Arg Arg Gly Gly Arg Pro Asp Phe Cys Leu Glu Pro Pro
1               5                   10                  15

Tyr Thr Gly Pro Cys Lys Ala Arg Ile Ile Arg Tyr Phe Tyr Asn Ala
            20                  25                  30

Lys Ala Gly Leu Cys Gln Thr Phe Val Tyr Gly Gly Cys Arg Ala Lys
        35                  40                  45

Arg Asn Asn Phe Lys Ser Ala Glu Asp Cys Xaa Arg Thr Cys Gly Gly
    50                  55                  60

Ala
65

<210> SEQ ID NO 34
<211> LENGTH: 7
<212> TYPE: PRT
<213> ORGANISM: Artificial
<220> FEATURE:
<223> OTHER INFORMATION: Synthesized
<220> FEATURE:
<223> OTHER INFORMATION: Peptide Tag

<400> SEQUENCE: 34

Thr Gly Arg Arg Arg Gly Gly
1               5
```

```
<210> SEQ ID NO 35
<400> SEQUENCE: 35

000

<210> SEQ ID NO 36
<211> LENGTH: 2
<212> TYPE: PRT
<213> ORGANISM: Artificial
<220> FEATURE:
<223> OTHER INFORMATION: Synthesized
<220> FEATURE:
<223> OTHER INFORMATION: GG linker

<400> SEQUENCE: 36

Gly Gly
1

<210> SEQ ID NO 37
<400> SEQUENCE: 37

000

<210> SEQ ID NO 38
<211> LENGTH: 8
<212> TYPE: PRT
<213> ORGANISM: Artificial
<220> FEATURE:
<223> OTHER INFORMATION: Synthesized
<220> FEATURE:
<223> OTHER INFORMATION: UBI 29-41 fragment comprising residues 5 to 13
      thereof

<400> SEQUENCE: 38

Arg Arg Met Gln Tyr Asn Arg Arg
1               5

<210> SEQ ID NO 39
<211> LENGTH: 5
<212> TYPE: PRT
<213> ORGANISM: Artificial
<220> FEATURE:
<223> OTHER INFORMATION: Synthesized
<220> FEATURE:
<223> OTHER INFORMATION: Peptide P15

<400> SEQUENCE: 39

Arg Arg Arg Gly Thr
1               5

<210> SEQ ID NO 40
<211> LENGTH: 8
<212> TYPE: PRT
<213> ORGANISM: Artificial
<220> FEATURE:
<223> OTHER INFORMATION: Synthesized
<220> FEATURE:
<223> OTHER INFORMATION: RC - 121
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (2)..(2)
<223> OTHER INFORMATION: Disulfide bond between this residue and
      residue 7
```

```
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (7)..(7)
<223> OTHER INFORMATION: Disulfide bond between this residue and
      residue 2

<400> SEQUENCE: 40

Phe Cys Tyr Trp Lys Val Cys Thr
1               5

<210> SEQ ID NO 41
<211> LENGTH: 15
<212> TYPE: PRT
<213> ORGANISM: Artificial
<220> FEATURE:
<223> OTHER INFORMATION: Synthesized
<220> FEATURE:
<223> OTHER INFORMATION: TGRRGG - RC - 121
<220> FEATURE:
<221> NAME/KEY: MISC_FEATURE
<222> LOCATION: (1)..(1)
<223> OTHER INFORMATION: Free N Terminus
<220> FEATURE:
<221> NAME/KEY: MISC_FEATURE
<222> LOCATION: (9)..(9)
<223> OTHER INFORMATION: Dilsulfide bond between this residue and
      residue 14
<220> FEATURE:
<221> NAME/KEY: MISC_FEATURE
<222> LOCATION: (14)..(14)
<223> OTHER INFORMATION: Dilsulfide bond between this residue and
      residue 9

<400> SEQUENCE: 41

Thr Gly Arg Arg Arg Gly Gly Phe Cys Tyr Trp Lys Val Cys Thr
1               5                   10                  15

<210> SEQ ID NO 42

<400> SEQUENCE: 42

000

<210> SEQ ID NO 43
<211> LENGTH: 11
<212> TYPE: PRT
<213> ORGANISM: Artificial Sequence
<220> FEATURE:
<223> OTHER INFORMATION: Synthesized
<220> FEATURE:
<223> OTHER INFORMATION: UBI 18-35 fragment

<400> SEQUENCE: 43

Lys Val Ala Lys Gln Glu Lys Lys Lys Lys
1               5                   10
```